United States Patent
Rourke et al.

(10) Patent No.: US 8,309,788 B2
(45) Date of Patent: Nov. 13, 2012

(54) PROTEASE INHIBITORS IN ABSORBENT ARTICLES

(75) Inventors: Francis James Rourke, Sharonville, OH (US); Scott Edward Osborne, Middletown, OH (US); Donald Carroll Roe, West Chester, OH (US); Todd Laurence Underiner, Cincinnati, OH (US); John McMillan McIver, Cincinnati, OH (US); Timothy Bates, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 134 days.

(21) Appl. No.: 12/358,697

(22) Filed: Jan. 23, 2009

(65) Prior Publication Data
US 2009/0131890 A1    May 21, 2009

Related U.S. Application Data

(63) Continuation of application No. 09/529,575, filed as application No. PCT/US99/05315 on Mar. 11, 1999, now abandoned.

(51) Int. Cl.
*A61F 13/15* (2006.01)

(52) U.S. Cl. .................................. 604/359; 604/360

(58) Field of Classification Search .................. 604/359, 604/360
See application file for complete search history.

(56) References Cited

U.S. PATENT DOCUMENTS

| | | | |
|---|---|---|---|
| 2,883,356 A | 4/1959 | Glusenkamp |
| 3,208,984 A | 9/1965 | Dekking |
| 3,489,148 A | 1/1970 | Duncan et al. |
| 3,585,998 A | 6/1971 | Hayford et al. |

(Continued)

FOREIGN PATENT DOCUMENTS

CA    2109557    12/1990

(Continued)

OTHER PUBLICATIONS

Uldall, Chr., "Comparative Studies on Feces of Healthy Breast-, Bottle- and Spoon-fed Infants", Report from the Laboratory of the Copenhagen Board of Health, Acta. Paediatr., vol. 29, pp. 339-366 (1942).

(Continued)

*Primary Examiner* — Lynne Anderson
(74) *Attorney, Agent, or Firm* — Megan C. Hymore; Amanda T. Barry

(57) ABSTRACT

The invention provides an absorbent article, at least a portion of which has a protease inhibitor incorporated therein to decrease the activity of proteases that may otherwise initiate or contribute to inflammation of the skin of a wearer of the article resulting in skin irritation or dermatitis. The article can further comprise a delivery system for releasably containing and delivering the protease inhibitor to at least a portion of the skin of the wearer. The delivery system can comprise a skin care composition and at least a portion of the composition, including the protease inhibitor, is automatically transferred from the article to the wearer's skin without manual intervention during normal usage of the article to form a defense against protease activity. Most preferably, repeated application of similarly treated articles to the wearer's skin provides an available source from which the protease inhibitor continuously transfers onto the skin over time and accumulates to provide a proactive defense against protease activity for the reduction or prevention of skin irritation or dermatitis due to proteolytic enzymes.

18 Claims, 2 Drawing Sheets

U.S. PATENT DOCUMENTS

| | | | |
|---|---|---|---|
| 3,707,148 A | 12/1972 | Bryce | |
| 3,875,942 A | 4/1975 | Roberts et al. | |
| 3,896,807 A | 7/1975 | Buchalter | |
| 3,920,015 A | 11/1975 | Wortham | |
| 3,935,862 A | 2/1976 | Kraskin | |
| 3,964,486 A | 6/1976 | Blaney | |
| 4,034,077 A | 7/1977 | Hill et al. | |
| 4,263,363 A | 4/1981 | Buck et al. | |
| 4,273,786 A | 6/1981 | Kraskin | |
| 4,401,712 A | 8/1983 | Morrison | |
| 4,450,151 A | 5/1984 | Shinozawa | |
| 4,556,560 A | 12/1985 | Buckingham | |
| 4,565,727 A | 1/1986 | Giglia et al. | |
| 4,569,343 A | 2/1986 | Kimura et al. | |
| 4,576,817 A | 3/1986 | Montgomery et al. | |
| 4,623,339 A | 11/1986 | Ciraldo et al. | |
| 4,657,537 A | 4/1987 | Zimmerer | |
| 4,666,765 A | 5/1987 | Caldwell et al. | |
| 4,685,909 A | 8/1987 | Berg et al. | |
| 4,690,821 A | 9/1987 | Smith et al. | |
| 4,707,293 A | 11/1987 | Ferro | |
| 4,753,643 A | 6/1988 | Kassai | |
| 4,790,836 A | 12/1988 | Brecher | |
| 4,795,740 A * | 1/1989 | Cohen et al. | 514/3.7 |
| 4,806,478 A | 2/1989 | Stahl | |
| 4,842,593 A | 6/1989 | Jordan et al. | |
| 4,861,584 A | 8/1989 | Powell, Jr. et al. | |
| 4,929,498 A | 5/1990 | Suskind et al. | |
| 4,959,059 A | 9/1990 | Eilender et al. | |
| 5,091,193 A | 2/1992 | Enjoiras et al. | |
| 5,110,593 A | 5/1992 | Benford | |
| 5,192,277 A | 3/1993 | Chung et al. | |
| 5,194,261 A | 3/1993 | Pichierri | |
| 5,362,488 A | 11/1994 | Sibley et al. | |
| 5,376,655 A | 12/1994 | Imaki et al. | |
| 5,409,903 A | 4/1995 | Polak et al. | |
| 5,415,649 A | 5/1995 | Watanabe et al. | |
| 5,417,981 A | 5/1995 | Endo et al. | |
| 5,436,007 A | 7/1995 | Hartung et al. | |
| 5,525,346 A | 6/1996 | Hartung et al. | |
| 5,607,760 A | 3/1997 | Roe | |
| 5,609,587 A | 3/1997 | Roe | |
| 5,612,045 A | 3/1997 | Syverson | |
| 5,618,529 A | 4/1997 | Pichierri | |
| 5,635,191 A | 6/1997 | Roe et al. | |
| 5,643,588 A | 7/1997 | Roe et al. | |
| 5,665,366 A * | 9/1997 | Rawlings et al. | 424/401 |
| 5,702,380 A | 12/1997 | Walker | |
| 5,856,245 A * | 1/1999 | Caldwell et al. | 442/76 |
| 5,869,033 A | 2/1999 | Schulz | |
| 5,874,164 A * | 2/1999 | Caldwell | 428/306.6 |
| 6,051,749 A | 4/2000 | Schulz | |
| 6,066,673 A | 5/2000 | McIver et al. | |
| 6,107,537 A | 8/2000 | Elder et al. | |
| 6,710,223 B1 | 3/2004 | Van Rijswijck et al. | |
| 6,803,496 B2 | 10/2004 | Elder et al. | |
| 6,861,571 B1 | 3/2005 | Roe et al. | |

FOREIGN PATENT DOCUMENTS

| | | | |
|---|---|---|---|
| DE | 4136540 | | 5/1992 |
| EP | 0 093 186 | | 11/1983 |
| EP | 0 555 116 | | 8/1993 |
| EP | 0 564 307 A1 | | 10/1993 |
| EP | 0 606 046 | | 7/1994 |
| EP | 0 682 868 | | 11/1995 |
| EP | 0 692 263 A2 | | 1/1996 |
| EP | 0 815 841 A1 | | 1/1998 |
| EP | 0 958 833 A1 | | 11/1999 |
| FR | 2660552 | | 10/1991 |
| FR | 2675341 | | 10/1992 |
| FR | 2700698 | | 11/1992 |
| FR | 2680448 | | 2/1993 |
| FR | 2714603 | | 7/1995 |
| GB | 2333703 A * | | 8/1999 |
| JP | 61028078 | | 2/1986 |
| JP | HEI2-31756 | | 2/1990 |
| JP | 04-182423 | | 6/1992 |
| JP | 8019595 | | 1/1996 |
| JP | 9-028730 | | 2/1997 |
| WO | WO 92/20319 | | 11/1992 |
| WO | WO 93/16681 | | 9/1993 |
| WO | WO 97/38735 | | 10/1997 |
| WO | WO 98/03147 | | 1/1998 |
| WO | WO 00/38625 | | 7/2000 |
| WO | WO 00/38626 | | 7/2000 |
| WO | WO 00/38747 | | 7/2000 |

OTHER PUBLICATIONS

White, C.M., "Cholestyramine Ointment to Treat Buttocks Rash and Anal Excoriation in an Infant", Ann Pharmacother, vol. 30, pp. 954-956 (Sep. 1996).

* cited by examiner

PROTEASE INHIBITORS IN ABSORBENT ARTICLES

CROSS REFERENCE TO RELATED APPLICATIONS

The application is a continuation of U.S. application Ser. No. 09/529,575, filed Apr. 14, 2000, now abandoned which is a National Stage Application of International Application No. PCT/US99/05315, filed Mar. 11, 1999, which claims priority to U.S. application Ser. No. 09/041,232, filed Mar. 12, 1998.

BACKGROUND OF THE INVENTION

The invention relates to absorbent articles such as diapers, training pants, adult incontinence briefs, feminine hygiene products, and the like. In particular, the absorbent articles of the invention contain fecal protease inhibitors and are useful for the prevention and treatment of diaper rash.

Diaper rash is a common form of irritation and inflammation of those parts of an infant's body normally covered by a diaper. This condition is also referred to as diaper dermatitis, napkin dermatitis, napkin rash and nappy rash. While certainly more common in infants, this condition is not, in fact, limited to infants. Any individual who suffers from incontinence to the extent that the use of absorbent articles is required may develop this condition. Susceptible individuals range from newborns, to the elderly, to critically ill, to non-ambulatory individuals.

Many types of disposable absorbent products, such as diapers, training pants, adult incontinence devices, sanitary napkins, panty liners, and the like, are available that have a high capacity for absorbing urine and other body exudates. Disposable products of this type generally comprise some sort of liquid-pervious topsheet material, an absorbent core, and a liquid-impervious backsheet material. Although these types of absorbent structures may be highly efficient for the absorption of liquids, it is well recognized that long-term wear of such absorbent articles may compromise the underlying skin in terms of overhydration or exposure to skin irritants commonly found in body exudates. Part 21, Section 333.503 of the Code of Federal Regulations defines diaper rash as "[a]n inflammatory skin condition in the diaper area (perineum, buttocks, lower abdomen, and inner thighs) caused by one or more of the following factors: moisture, occlusion, chafing, continued contact with urine or feces or both, or mechanical or chemical irritation." It is generally accepted by the medical profession that true diaper rash or diaper dermatitis is a condition which is, in its most simple stages, a contact irritant dermatitis resulting from extended contact of the skin with urine, or feces, or both. Among the most commonly accepted factors linked to diaper rash are ammonia, fecal enzymes, bacteria, the products of bacterial action, urine pH, and *Candida albicans*.

As discussed in Buckingham, U.S. Pat. No. 4,556,560; Zimmerer, U.S. Pat. No. 4,657,537; Berg and Stewart, U.S. Pat. No. 4,685,909; Jordan and Ryan, U.S. Pat. No. 4,842,593; Andersen et al. (Contact Dermatitis 30:152-158, 1994); MacFarlane et al. (J. Appl. Bacteriol. 64:37-46, 1988); and Buckingham and Berg, (Pediatric Dermatology 3:107-112, 1986), there is evidence that fecal proteolytic and lipolytic enzymes, of intestinal and/or pancreatic origin, play a direct role in causing the skin irritation and inflammation of diaper rash. Studies with inhibitors designed to inhibit the enzymatic activity of various classes of proteases showed that serine proteases, cysteine proteases and metalloproteases were the most likely to be responsible for the overall proteolytic activity of feces. It is known that the serine proteases trypsin and chymotrypsin, in particular, are nearly always present in grossly measurable quantities in the stools of normal young children, and smaller but detectable quantities are present in normal adult stools.

The irritating effects of fecal enzymatic activity toward the skin are likely to be amplified if urine is present and/or if the skin is occluded. The production of ammonium hydroxide by the action of the bacterial enzyme urease on urine results in an increase in pH, for example to levels of 7.0 and above, at which the enzymatic activity of proteases and other enzymes such as lipases present in feces is enhanced. For example, the optimal pH range for urease activity is 6.4-6.9, for trypsin 7.8 to 8.2, and for lipases 7.5-9.5. At a pH greater than 7.0, free ammonia is released from urine as a toxic additional skin irritant. Urine itself can also contribute to diaper rash by adding moisture to the diaper environment. Water, and particularly water in the form of urine, is especially effective at diminishing the barrier property of skin, thereby enhancing the susceptibility of skin to fecal enzyme irritation. Since urine and feces are commonly present in the absorbent article at the same time, and exposure to the skin for several hours is not uncommon, suitable conditions and ample time are available for this interaction and the resulting skin damage to occur. An alkaline feces pH is a further contributing factor to enhanced enzymatic activity of feces. For example, it is well known that although the feces of breast-fed babies are usually acidic, the feces of bottle-fed and spoon-fed infants are generally alkaline, with a pH ranging from slightly alkaline (pH 7.2-7.5) to very alkaline (pH 8.7 and above). Thus bottle-fed and spoon-fed infants in particular may have a propensity to develop diaper rash due to pH-enhanced activity of fecal enzymes.

In view of the foregoing proposed causes of diaper rash, many approaches have been taken in an attempt to reduce or prevent its occurrence. Many of the most practical approaches attempt to address multiple causes or important cofactors. Reducing skin hydration by frequent changing of diapers, the use of moisture absorbing powders, the use of superabsorbent materials, and improving air flow in diapers are well known approaches. The use of artificial barriers is also widely practiced. Typical of these is the use of a topical cream, ointment, lotion or paste to provide some degree of physical barrier protection to the skin against fecal or urine irritants, regardless of their specific nature. However, the barrier approach, while reducing access of irritants to the skin, may be occlusive in itself and can be aesthetically unpleasing.

In another approach, attempts have been made to maintain skin pH by the use of pH control agents, such as buffering agents or acidic ammonia-neutralizing agents, in an absorbent article or as ingredients in topically applied skin care products. It is thought that effectively maintaining skin pH in its natural acidic state (i.e., about 3.0 to about 5.5) may counteract the irritating effects of ammonia and reduce the activity of fecal enzymes. Reducing the enzymatic activity on the skin by this approach, however, is potentially difficult in the situation where alkaline feces are deposited directly on the skin following a bowel movement.

Certain anti-enzyme compounds have been included in topically applied compositions for treatment or prevention of diaper rash caused by the prolonged contact of human skin with body wastes. For example, U.S. Pat. No. 4,556,560 describes compositions containing water-soluble lipase inhibitors that are preferably metallic salts such as zinc chloride in a barrier-like carrier such as polyethylene glycol. U.S. Pat. No. 5,091,193 describes compositions for application to the skin at the time of diaper change that contain a chelating agent such as phytic acid, ethylenediamine tetraacetic acid, (EDTA) and the like, that restricts the availability of metals that ureases and proteases require as cofactors for activity. The composition may further include a lipase inhibitor such as an ester of a fatty alcohol or an additional anti-enzyme, such as a saturated or unsaturated, linear or branched zinc salt of a fatty acid of 2 to 22 carbon atoms or an aminated acylated acid such as propionylcysteine, propionylhydroxyproline or caproylcysteine. Cleaning wipes having skin cleaner compositions that incorporate protease inhibitors have also been described for use in place of toilet paper for cleansing body excreta from the skin to prevent irritation.

Although there appear to be multiple factors involved in the development of diaper rash, it is likely that the physiological responses of the skin to irritants such as fecal enzymes, ammonia, and the like, may involve some common mechanisms. For example, it is known that the production of cytokines by skin cells is a common response to the presence of irritants and to perturbation of the outer barrier layer of the skin (the stratum corneum). The principal cell type that appears to be involved in the production of cytokines is the keratinocyte, which is the cell type found directly beneath the stratum corneum and is the most likely to initially encounter an irritant. It has been demonstrated that the keratinocyte secretes a wide variety of different cytokines, including the proinflammatory cytokine interleukin 1-alpha (IL-1α), in response to irritants. This cytokine and others induce a cascade of events which may eventually lead to the physiological appearance of erythema, papules, scaling and ulceration which are collectively described as diaper dermatitis.

While compositions for the treatment or prevention of diaper rash have been described that include certain inhibitors of urease, lipase and/or protease enzyme activity, it has not been previously recognized that fecal proteases play an important role in inducing the initial cytokine response of keratinocytes leading to the inflammatory response cascade and that the inhibition of proteases, in particular, provides a more specific means of preventing or treating diaper rash than previously disclosed. In particular, there has been no previous description of a treatment regimen for the reduction or prevention of diaper dermatitis by which protease inhibitors are incorporated directly into absorbent articles such as diapers and the like, or that effective amounts of the protease inhibitors may be delivered automatically to a wearer's skin from the treated articles without manual intervention. Further, it has not been previously recognized that the use, preferably the repeated use, of treated absorbent articles may automatically transfer sufficient levels of the protease inhibitors to selected regions of the wearer's skin to provide a proactive defense against fecal protease penetration and activity.

SUMMARY OF THE INVENTION

The invention provides an absorbent article, at least a portion of which has a protease inhibitor incorporated therein to decrease the activity of proteases that may otherwise initiate or contribute to inflammation of the skin of a wearer of the article resulting in skin irritation or dermatitis. As used in the context of the invention, the term "protease inhibitor" means any substance that inhibits protease activity in one or more of the seven assays described below at (i) an $IC_{50}$, as defined below, of about 30 micromolar (µM) or less, typically about 0.00001 µM to about 30 µM, more typically about 0.0001 µM to about 20 µM, still more typically about 0.001 µM to about 10 µM, and most typically about 0.01 µM to about 5 µM, as measured by a Purified Protease Method described below; (ii) at an $IC_{50}$ of about 90 µM or less, typically about 0.00001 µM to about 90 µM, more typically about 0.0001 µM to about 30 µM, still more typically about 0.001 µM to about 10 µM, and most typically about 0.01 µM to about 5 µM, as measured by a Specific Fecal Protease Method described below; or (iii) at an $IC_{50}$ of less than about 500 µM, more typically less than about 300 µM, and still more typically less than about 100 µM as measured by a General Fecal Protease Method described below.

The protease inhibitor incorporated into the article of the invention preferably inactivates one or more of the major types of proteases present in feces, i.e., serine proteases, metalloproteases, cysteine proteases, and aspartyl proteases. Although any protease inhibitor or mixture of protease inhibitors that meets the $IC_{50}$ criteria stated above may be employed in the absorbent article, it has been discovered and demonstrated herein that inhibition of serine protease activity in feces by the use of a serine protease inhibitor such as soybean trypsin inhibitor and hexamidine, in particular, significantly reduces the initial cytokine response by skin cells to feces. Exemplary suitable protease inhibitors for use in the absorbent articles of the invention include soybean trypsin inhibitor and hexamidine, as well as aprotinin, p-aminobenzamidine, leupeptin, pepstatin A, chymostatin, and the like.

The article preferably comprises about 0.0001% to about 30%, preferably 0.0001% to about 10%, by weight of the protease inhibitor. The inhibitor may be present neat, such as a powder, flakes, particles and the like, or may be in a carrier vehicle as a solution, suspension, dispersion, emulsion and the like. Moreover, the inhibitor may be releasably contained by a microcapsule, an absorbent material, a cell, an adhesive, a skin care composition, a solid support, a nanophase particulate structure, and the like. Preferably the inhibitor in the absorbent article reduces protease activity, as measured by the Absorbent Article Test Method (described below), by at least about 10%, more preferably by at least about 20%, even more preferably by at least about 50%, and most preferably by at least about 80%. Typically the inhibitor in the absorbent article reduces protease activity by about 10% to about 99%, more typically by about 20% to about 99%, even more typically by about 50% to about 99%, and most typically by about 80% to about 99%.

The absorbent article preferably further comprises a delivery system for releasably containing and delivering the protease inhibitor to at least a portion of the skin of the wearer of the article. The delivery system may be of any configuration including, but not limited to, one that contains the protease inhibitor in powder, particle or flake form, or in a solution, a dispersion, a suspension, an emulsion, or the like. The delivery system may comprise a structure such as a microcapsule, an absorbent material, a nanophase particulate structure, a cell, an adhesive, a solid support, or the like, or a composition such as a skin care composition. Preferably, the delivery system positions the protease inhibitor in proximity to the skin during wear of the article and, more preferably, onto at least a portion of the skin of the wearer of the article, such that the inhibitor can intercept fecal proteases at the skin/feces interface before they can penetrate to the surface of the stratum corneum of the skin, thereby reducing or preventing activation of an inflammatory response.

In a preferred embodiment of the invention, the delivery system comprises a skin care composition that contains about 0.01% to about 50%, preferably about 0.05% to about 25%, especially about 0.1% to about 10%, by weight of the protease inhibitor. More preferably, at least a portion of a wearer-contacting surface of the absorbent article comprises the inhibitor-containing skin care composition such that a portion of the skin care composition including the protease inhibitor is automatically transferred from the article to the wearer's skin without manual intervention during normal usage of the article to form a defense against fecal proteases at the skin-feces interface. Most preferably, repeated application of similarly treated articles to the wearer's skin provides an available source from which the protease inhibitor continuously transfers onto the skin over time and accumulates to provide a proactive defense against fecal proteases for the reduction or prevention of diaper dermatitis due to proteolytic enzymes.

An advantage of the protease inhibitor-treated absorbent articles of the invention is that inhibition of fecal proteases and, therefore, reduction of the skin irritation due to contact with feces, is a direct result of the inhibitor-enzyme interaction, rather than by any indirect means, such as a change in pH, the inactivation of a cofactor required for enzyme activity, or the presence of other skin health-enhancing compounds. By the judicious selection of inhibitors which inactivate the major types of proteases present in feces, a method for the treatment and/or prevention of diaper dermatitis is established that requires a very low amount of the protease inhibitor in the article. Moreover, the inhibitor-enzyme interaction of the invention is accomplished at high pH levels normally found in soiled diapers and other absorbent articles under non-buffered conditions.

DETAILED DESCRIPTION OF THE INVENTION

I. Definitions

Figure 1:
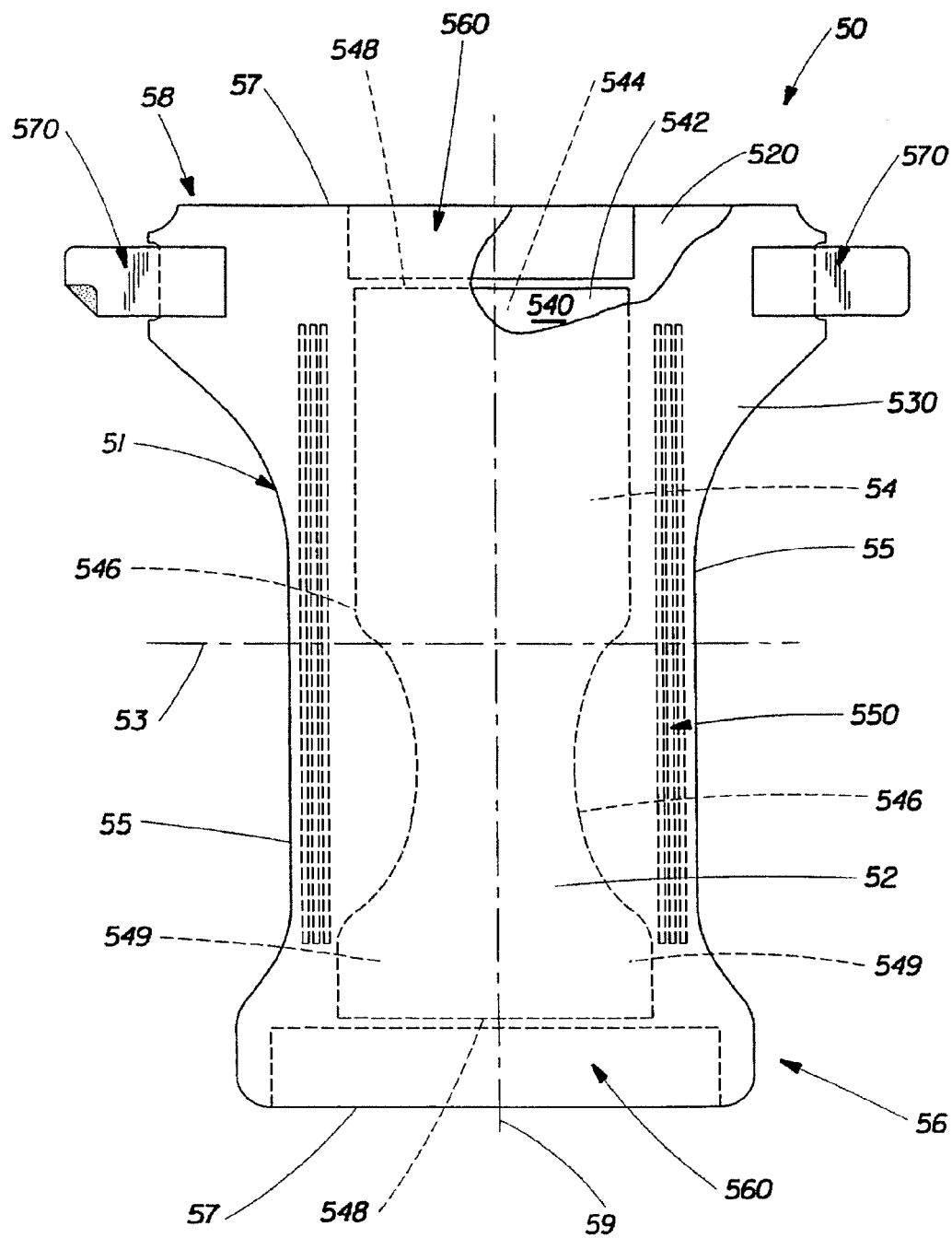
FIG. 1 is a schematic illustration of an absorbent article in the form of a diaper according to the present invention.

As used herein, the term "comprising" means that the various components, ingredients, or steps can be conjointly employed in practicing the present invention. Accordingly, the term "comprising" encompasses the more restrictive terms "consisting essentially of" and "consisting of".

As used herein, the term "$IC_{50}$" means the inhibitory concentration (e.g., a micromolar concentration, µM) of a substance (inhibitor) which reduces the rate of substrate cleavage by a protease by 50%, as measured by the standard in vitro protease activity assays described below. The $IC_{50}$ is calculated according to the equation $IC_{50}=[I]/[(v/v_i)-1]$, where [I] is the inhibitor concentration tested, v is the rate of substrate cleavage in the absence of the inhibitor and $v_i$ is the rate of substrate cleavage in the presence of the inhibitor. As described further below, the $IC_{50}$ of a protease inhibitor according to the invention may be measured by a Purified Protease Method, by a Specific Fecal Protease Method, or by a General Fecal Protease Method.

Other terms are defined herein where initially discussed.

All percentages, ratios and proportions used herein are by weight unless otherwise specified.

II. The Invention

The invention provides an absorbent article which contains a protease inhibitor that inhibits one or more proteases found in feces and meets any one of the $IC_{50}$ criteria for inhibitory activity against trypsin, chymotrypsin and/or leucine aminopeptidase in a Purified Protease assay, a Specific Fecal Protease assay or a General Fecal Protease assay described below. More particularly, the invention provides an absorbent article which contains a protease inhibitor having an $IC_{50}$ of about 30 µM or less, typically about 0.00001 µM to about 30 µM, more typically about 0.0001 µM to about 20 µM, still more typically about 0.001 µM to about 10 µM, and most typically about 0.01 µM to about 5 µM as measured by the Purified Protease Method. The invention separately provides an absorbent article which contains a protease inhibitor having an $IC_{50}$ of about 90 µM or less, typically about 0.00001 µM to about 90 µM, more typically about 0.0001 µM to about 30 µM, still more typically about 0.001 µM to about 10 µM, and most typically about 0.01 µM to about 5 µM as measured by the Specific Fecal Protease Method. The invention additionally provides an absorbent article which contains a protease inhibitor or a mixture of protease inhibitors having an $IC_{50}$ of less than about 500 µM, more typically less than about 300 µM, and still more typically less than about 100 µM as measured by the General Fecal Protease Method. As used in the context of the invention, the term "treated article" refers to an absorbent article containing the protease inhibitor. In one embodiment of the invention, the protease inhibitor is initially available in or is migratable to a portion of the absorbent article which may come in contact with feces, especially runny feces, for direct inhibition of fecal protease activity in that portion of the article. As discussed below, the inhibitor may be initially in an active form or it may be initially inactive but activatable by, for example, an extraneous source such as moisture from urine or feces.

In another embodiment of the invention, the absorbent article comprises a delivery system that contains a protease inhibitor and that automatically, without manual intervention, delivers an effective amount of the inhibitor to at least a portion of the skin of a wearer during wear of the article for the inhibition of fecal proteases at the skin/feces barrier. More preferably, the use or the repeated use of similar articles having protease inhibitor delivery systems automatically transfers a sufficient level of the protease inhibitor to selected regions of the wearer's skin prior to contact with feces to provide a proactive defense against fecal protease penetration and activity.

It is theorized that fecal proteases break down proteinaceous substances present in the stratum corneum (outer barrier layer) of the skin, resulting in cytokine production by underlying keratinocytes and activation of an inflammatory response cascade that produces symptoms of diaper rash. As demonstrated herein, the protease inhibiting substances for use in the absorbent articles of the present invention have a surprising ability to inhibit the induction of cytokine production by keratinocytes in the presence of feces that is due to a direct inhibitor-enzyme interaction. While not intending to be bound or limited by theory, it is thought that the presence of a protease inhibitor meeting the $IC_{50}$ criteria for activity described above that is in contact with feces within the article or at the skin/feces interface reduces or prevents the occurrence of an initial insult by a fecal protease to the stratum corneum. Therefore, an absorbent article having a protease inhibitor incorporated therein or preferably having a delivery system that delivers the protease inhibitor in an effective concentration directly onto the skin is useful in the treatment and/or prevention of diaper dermatitis.

It is well known that one of the most important functions of the skin is to act as a barrier to the egress of physiologic fluids, electrolytes and other components, as well as to act as a barrier to the ingress of microbes, toxins, and other inflammatory or harmful agents. In light of the discovery that fecal proteases contribute significantly to diaper dermatitis, it is thought that in addition to causing skin irritation by the digestive degeneration of the stratum corneum, the action of compromising this barrier allows other components of urine and feces, ammonia, fatty acids and the like which may not otherwise be irritating by themselves, to migrate through the compromised skin barrier to produce additional irritation. For example, *Candida albicans*, which produces an aspartyl protease, is frequently found as a major component of human feces in individuals treated with antibiotics. This yeast thrives in moist environments found in soiled diapers and, if the skin barrier is perturbed, not only can the aspartyl protease contribute to further breakdown of the skin, but a serious *Candida* infection could occur. Therefore, inclusion of inhibitors of fecal proteases in absorbent articles, as described herein, helps to maintain the integrity of the stratum corneum barrier and effectively prevents the occurrence of secondary irritation and/or infection that can contribute to diaper dermatitis.

III. Protease Inhibitors

Protease is a common term employed to represent a group of proteolytic enzymes that are capable of splitting proteins and peptides into fragments by cleaving or hydrolyzing peptide bonds. Proteases can be subclassified into proteinases (endopeptidases) and the peptidases (exopeptidases). Peptidases act on peptide bonds adjacent to a free amino or carboxyl group on the end of a protein and thus cleave the protein from the outside. Among the principal types of peptidases are carboxypeptidases, dipeptidases and aminopeptidases. Proteinases act on specific interior peptide bonds of proteins and can be subclassified into four kinds, i.e. serine proteases, metalloproteases, cysteine proteases, and aspartyl proteases. Among the principal types of proteinases are trypsin and chymotrypsin. Because proteases are widely distributed in plants, molds, bacteria, milk, milk products, and almost all animal tissues, as well as in digestive juices in the gastrointestinal tract, they are almost always present in the diapered area when it has been soiled by human waste. Each of the protease inhibitors included in the absorbent articles of the invention is a chemical substance which meets at least one of the seven criteria for $IC_{50}$ described above and reversibly or irreversibly inhibits the hydrolytic action of one or more proteases included among the foregoing functional subclasses of proteases normally found in human feces as well as among proteases whose substrate specificity is as yet undefined.

Protease inhibitors that may be employed in the embodiments of the invention include any naturally occurring inhibitor of plant, microbial and/or animal origin (including human), and synthetically manufactured chemical inhibitor that meets the criteria for $IC_{50}$ described above. Exemplary protease inhibitors that are believed to meet the $IC_{50}$ criteria and are further believed to inhibit the type of protease indicated in parentheses include, but are not limited to, soybean trypsin inhibitor and other plant-derived trypsin inhibitors such as lima bean protease inhibitor, corn protease inhibitor and the like; Bowman Birk inhibitor (serine, trypsin-like protease inhibitor); pancreatic trypsin inhibitor such as bovine pancreatic basic trypsin inhibitor and other animal-derived pancreatic trypsin inhibitors; egg white trypsin inhibitor (serine, trypsin-like protease inhibitor); ovomucoids containing ovoinhibitors such as from chicken or turkey egg white (trypsin and chymotrypsin inhibitors); chymostatin (serine, chymotrypsin-like protease inhibitor); aprotinin (serine protease inhibitor); leupeptin and its analogs such as propionyl-leupeptin, N-α-t-BOC-deacetylleupeptin (serine and cysteine protease inhibitor); bestatin and its analogs such as epibestatin and nitrobestatin (aminopeptidase metalloprotease inhibitor); amastatin and its analogs such as epiamastatin (aminopeptidase inhibitor); antipain (trypsin inhibitor); antithrombin III (serine protease inhibitor); 4-sulfamoylphenyl-4-guanidinobenzoate methanesulfonate (trypsin inhibitor); camostat (trypsin inhibitor); elafin (elastase inhibitor); hirudin (thrombin-like serine protease inhibitor); cystatin (egg white cysteine protease inhibitor); E-64 (trans-epoxysuccinyl-L-leucylamido-(4-guanidino)-butane) and its analogs (cysteine protease inhibitor); $\alpha_2$-macroglobulin (universal endoprotease inhibitor); $\alpha_1$-antitrypsin (trypsin inhibitor); pepstatin and its analogs such as acetyl pepstatin, pepstatin A, Nle-Sta-Ala-Sta (aspartyl protease inhibitor); apstatin (aminopeptidase P inhibitor); (2R)-2-mercaptomethyl-4-methylpentanoyl-b-(2-naphthyl)-Ala-Ala amide (matrix metalloprotease inhibitor); (2R)-2-mercaptomethyl-4-methylpentanoyl-Phe-Ala amide (matrix metalloprotease inhibitor); N-acetyl-Leu-Leu-methioninal (calpain inhibitor); N-acetyl-Leu-Leu-norleucinal (calpain inhibitor); p-aminobenzoyl-Gly-Pro-$_D$-Leu-$_D$-Ala hydroxamic acid (matrix metalloprotease inhibitor); 2(R)-[N-(4-methoxyphenylsulfonyl)-N-(3-pyridylmethyl)amino]-3-methylbutano-hydroxamic acid (metalloprotease inhibitor); 4-(2-aminoethyl)-benzenesulfonylfluoride hydrochloride (broad spectrum/general protease inhibitor); and mixtures of any of the foregoing.

Among preferred protease inhibitors for use in the absorbent articles of the invention are compounds that exhibit inhibitory activity that is not necessarily restricted to a single class of proteases. Such compounds include, but are not limited to, hexamidine and its salts; pentamidine and its salts; benzamidine and its salts and derivatives, p-aminobenzamidine and its salts and derivatives; and guanidinobenzoic acid and its salts and derivatives such as those disclosed in U.S. Pat. No. 5,376,655 issued to Imaki et al. on Dec. 27, 1994, the disclosure of which is hereby incorporated by reference. Other preferred protease inhibitors include polymer derivatives of guanidinobenzoic acid disclosed and made in our co-pending U.S. patent application Ser. No. 09/041,196, filed Mar. 12, 1998 in the name of T. L. Underiner et al, co-filed with the present application, the disclosure of which co-pending application is hereby incorporated by reference.

The protease inhibitors may be employed singly or as a mixture of protease inhibitors such as a "cocktail" of inhibitors in a single absorbent article. Moreover, different protease inhibitors may be employed in different locations in a single absorbent article.

Because of the wide diversity of enzymes present in feces, it is reasonably predictable that materials such as those described above which inhibit fecal proteases may also inhibit enzymes that cleave substrates other than proteins and peptides. Hence protease inhibitors which also inhibit lipases and other esterases, amylases, and/or ureases are within the scope of the embodiments of the invention if the inhibitor meets the $IC_{50}$ criteria for protease inhibitory activity as described above.

Protease inhibitors that are preferred in the practice of the invention are soybean trypsin inhibitor, Bowman-Birk inhibitor, aprotinin, hexamidine (e.g., hexamidine diisethionate), p-aminobenzamidine, leupeptin, pepstatin A, chymostatin and polymer derivatives of guanidinobenzoic acid (disclosed and made in our copending U.S. patent application Ser. No. 09/041,196, incorporated by reference above. Particularly preferred protease inhibitors are soybean trypsin inhibitor, hexamidine, p-aminobenzamidine and the foregoing polymer derivatives of guanidinobenzoic acid.

IV. Absorbent Articles

As used herein, the term "absorbent article" refers to a device which absorbs and retains body exudates. The term "disposable" is used herein to describe absorbent articles which are not intended to be laundered or otherwise restored or reused as an absorbent article after a single use. Examples of disposable absorbent articles include feminine hygiene garments such as sanitary napkins, panty liners, diapers, incontinence briefs, incontinence pads, diaper holders, training pants, and the like.

Protease inhibitors may be incorporated into any portion or portions of any of the absorbent articles described herein. Delivery systems for the protease inhibitors are components of the absorbent articles and are discussed separately below.

Disposable absorbent articles typically comprise a liquid pervious topsheet, a liquid impervious backsheet and an absorbent core positioned between the topsheet and the backsheet. Disposable absorbent articles and components thereof, including the topsheet, backsheet, absorbent core, and any individual layers of these components, have a body facing surface and a garment facing surface. As used herein "body facing surface" means that surface of the article or component which is intended to be worn toward or adjacent to the body of the wearer, while the "garment facing surface" is on the opposite side and is intended to be worn toward or placed adjacent to the wearer's clothing or undergarments when the disposable absorbent article is worn.

The following description generally discusses the absorbent core, topsheet, and backsheet materials that are useful in disposable absorbent articles. It is to be understood that this general description applies to these components of the specific absorbent articles shown in FIG. 1 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to absorbent composites, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers including composites; absorbent gelling materials; or any equivalent material or combinations of materials, or mixtures of these.

The configuration and construction of the absorbent core may be varied (e.g., the absorbent core may have varying caliper zones and/or have a profile so as to be thicker in the center; hydrophilic gradients; gradients of absorbent composites; superabsorbent gradients; or lower average density and lower average basis weight zones, e.g., acquisition zones; or may comprise one or more layers or structures). The total absorbent capacity of the absorbent core should however, be compatible with the design loading and the intended use of the absorbent article. Further, the size and absorbent capacity of the absorbent core may be varied to accommodate different uses such as diapers, incontinence pads, panty liners, regular sanitary napkins, and overnight sanitary napkins, and to accommodate wearers ranging from infants to adults. The absorbent core can also include other absorbent components that are often used in absorbent articles, for example, a dusting layer, a wicking or acquisition layer such as a high loft acquisition layer for temporary holding of urine, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured plastic films (e.g., hydroformed thermoplastic films); porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, spunlace carded, wet-laid, melt-blown, hydroentangled, hydroformed, hydroapertured, combinations of the above, or the like. Whether comprised of a woven or nonwoven material, the topsheet preferably comprises a skin care composition containing a protease inhibitor, as described further below.

The backsheet is impervious to liquids (e.g., menses and/or urine) and preferably comprises a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent the garment facing surface and the body facing surface, respectively, of the absorbent core. The absorbent core is preferably joined with the topsheet, the backsheet, or both in any manner as is known by attachment means (not shown in FIG. 1) such as those well known in the art. However, embodiments of the absorbent articles are envisioned wherein portions or the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern as illustrated by the apparatus and method shown in U.S. Pat. No. 3,911,173, issued to Sprague, Jr. on Oct. 7, 1975; U.S. Pat. No. 4,785,996, issued to Zwieker et al. on Nov. 22, 1978; and U.S. Pat. No. 4,842,666, issued to Werenicz on Jun. 27, 1989. Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article of the invention, at least a portion of which has a protease inhibitor and/or a delivery system for a protease inhibitor incorporated therein and, more preferably, has a wearer-contacting surface treated with a skin care composition containing a protease inhibitor, is a diaper. As used herein, the term "diaper" refers to an absorbent article generally worn by infants, and incontinent persons, that is worn about the lower torso of the wearer. In other words, the term "diaper" includes infant diapers, training pants, adult incontinence devices and the like.

FIG. 1 is a plan view of the diaper 50 useful in the invention in its flat-out, uncontracted state (i.e., with elastic induced contraction pulled out) with portions of the structure being cut-away to more clearly show the construction of the diaper 50 and with the portion of the diaper 50 which faces away from the wearer (the outer surface) oriented towards the viewer. As shown in FIG. 1, the diaper 50 preferably comprises a liquid pervious topsheet 520, a liquid impervious backsheet 530 joined with the topsheet 520, an absorbent core 540 positioned between the topsheet 520 and the backsheet 530, the absorbent core 540 having a garment facing surface 542, a body facing surface 544, side edges 546, waist edges 548, and ears 549. The diaper 50 preferably further comprises elasticized leg cuffs 550, and elastic waist feature multiply designed as 560, and a fastening system generally multiply designed as 570.

The diaper 50 is shown in FIG. 1 to have an outer surface 52, an inner surface 54 corresponding to the body facing surface which is opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The body facing surface 54 of the diaper 50 comprises that portion of the diaper 50 which is positioned adjacent to the wearer's body during use. The body facing surface 54 generally is formed by at least a portion of the topsheet 520 and other components that may be joined to the topsheet 520, such as leg cuffs 550, as well as any regions to which the topsheet may not extend but which still contact the wearer, such as the waist feature 560, side panels, and the like. The outer surface 52 comprises that portion of the diaper 50 which is positioned away from the wearer's body (i.e., the outer surface 52 generally is formed by at least a portion of the backsheet 530 and other components that may be joined to the backsheet 530). The first waist region 56 and the second waist region 58 extend, respectively, from the end edges 57 of the periphery 51 to the lateral centerline 53 of the diaper 50. FIG. 1 also shows the longitudinal centerline 59.

FIG. 1 shows a preferred embodiment of the diaper 50 in which the topsheet 520 and the backsheet 530 have length and width dimensions generally larger than those of the absorbent core 540. The elasticized leg cuffs 550 and the backsheet 530 extend beyond the edges of the absorbent core 540 to thereby form the periphery 51 of the diaper 50.

Diapers of the present invention can have a number of well known configurations, with the absorbent cores thereof being adapted to the present invention. Exemplary configurations are described generally in U.S. Pat. No. 3,860,003, issued to Buell on Jan. 14, 1975; U.S. Pat. No. 5,151,092, issued to Buell et al. on Sep. 29, 1992; U.S. Pat. No. 5,221,274 issued to Buell et al. on Jun. 22, 1993. Each of these patents is incorporated herein by reference. Another diaper configuration to which the present invention can be readily adapted is described in U.S. Pat. No. 5,554,145 issued to Roe et al., the disclosure of which is incorporated herein by reference.

A topsheet 520 which is particularly suitable for use in the diaper 50, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophilic material to promote rapid transfer of liquids (e.g., urine) through the topsheet. If the topsheet is made of a hydrophobic material, at least portions of the upper surface of the topsheet are treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. Nos. 4,988,344 and 4,988,345, both issued to Reising, et al. on Jan. 29, 1991, each of which is incorporated by reference herein.

Alternatively, the topsheet may be in the form of an apertured formed film, which is preferred in feminine hygiene absorbent articles. Apertured formed films are useful because they are pervious to body liquids and yet non-absorbent and have a reduced tendency to allow liquids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents is incorporated herein by reference. Particularly preferred microapertured formed film topsheets are disclosed in U.S. Pat. No. 4,609,518 issued to Curro et al. on Sep. 2, 1986 and U.S. Pat. No. 4,629,643 issued to Curro et al. on Dec. 16, 1986, which are hereby incorporated by reference. The preferred topsheet for use in feminine hygiene products is the formed film described in one or more of the above patents and marketed on sanitary napkins by The Procter & Gamble Company of Cincinnati, Ohio as "DRI-WEAVE®."

The body facing surface of the formed film topsheet can be hydrophilic so as to help body liquids to transfer through the topsheet faster than if the body surface were not hydrophilic so as to diminish the likelihood that liquid will flow off the topsheet rather than flowing into and being absorbed by the absorbent structure. In a preferred embodiment, surfactant is incorporated into the polymeric materials of the formed film topsheet such as is described in U.S. Statutory Invention Registration H1670 to Aziz et al., published Jul. 1, 1997, which is hereby incorporated by reference. In alternative embodiments (not shown) of the present invention, the absorbent article may be provided with means for improving contact between the topsheet and a wearer's skin. In one such embodiment, the absorbent article can be provided with elastic means, as described in U.S. Pat. No. 4,892,536 issued in the name of DesMarais, et al. on Jan. 9, 1990, in U.S. Pat. No. 4,990,147, issued in the name of Freeland on Feb. 5, 1991, and in U.S. patent application Ser. No. 07/993,198, filed in the name of Freeland, et al. on Dec. 18, 1992, which lift the topsheet to improve contact with a wearer's perianal region. In another embodiment, described in U.S. Pat. No. 5,171,236, issued in the name of Dreier, et al. on Dec. 15, 1992, a diaper is provided with spacing means to lift the topsheet. In yet another embodiment, described in U.S. Statutory Invention Registration H1687, published in the name of Roe, et al. on Oct. 7, 1997, the absorbent article is provided with a gluteal blocking device which lifts the topsheet into a wearer's gluteal groove.

In a preferred embodiment of a diaper as described herein, the backsheet 530 has a modified hourglass shape extending beyond the absorbent core a minimum distance of about 1.3 cm to about 6.4 cm (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent materials for use as the absorbent core of articles useful in the present methods are described, e.g., in U.S. Pat. No. 4,610,678 issued to Weisman et al. on Sep. 9, 1986; U.S. Pat. No. 4,673,402 issued to Weisman et al. on Jun. 16, 1987; U.S. Pat. No. 4,888,231 issued to Angstadt on Dec. 19, 1989; and U.S. Pat. No. 4,834,735 issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423 issued to Alemany et al., on Aug. 10, 1993; and in U.S. Pat. No. 5,147,345 issued to Young, LaVon and Taylor on Sep. 15, 1992. All of these patents are hereby incorporated by reference.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized waist bands (not shown) and/or elasticized side panels (also not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in U.S. Pat. Nos. 3,860,003; 4,909,803 issued to Aziz et al. on Mar. 20, 1990; U.S. Pat. No. 4,695,278 issued to Lawson on Sep. 22, 1987; and U.S. Pat. No. 4,795,454 issued to Dragoo on Jan. 3, 1989, the disclosure of each of which is hereby incorporated by reference. Absorbent articles having elasticized cuffs that are treated with a composition that may be useful herein are disclosed in co-pending U.S. patent application Ser. Nos. 08/766,386 and 08/840,039, filed Dec. 3, 1996 and Apr. 24, 1997, respectively, the disclosures of both of which are hereby incorporated by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, the disclosures of each of these references being hereby incorporated by reference.

The elasticized side panels may be constructed in a number of configurations. Examples of diapers with elasticized side panels positioned in the ears (ear flaps) of the diaper are disclosed in U.S. Pat. No. 4,857,067 issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and U.S. Pat. No. 5,151,092 issued to Buell et al. on Sep. 29, 1992; the disclosures of each of which are hereby incorporated by reference.

Exemplary fastening systems 570 are disclosed in U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; U.S. Pat. No. 3,848,594 issued to Buell on Nov. 19, 1974; U.S. Pat. No. 4,662,875 issued to Hirotsu et al. on May 5, 1987; and U.S. Pat. No. 5,151,092 issued to Buell et al. on Sep. 29, 1992; the disclosures of each of which are hereby incorporated by reference.

The diaper 50 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

Of course, it will be recognized that any absorbent article design may be utilized in the present invention to incorporate a protease inhibitor and/or a delivery system for delivering the inhibitor onto the skin of a wearer during wear of the article, as described below. The disclosure above is merely for illustrative purposes.

The present invention may also employ training pants as an absorbent article comprising a protease inhibitor. The term "training pants", as used herein, refers to disposable garments having fixed sides and leg openings designed for infant or adults wearers. Training pants (also referred in the art as "pull on" products) are placed in position on the wearer by inserting the wearer's legs into the leg openings and sliding the training pant into position about the wearer's lower torso. Suitable training pants are disclosed in U.S. Pat. No. 5,246,433 issued to Hasse, et al. on Sep. 21, 1993, U.S. Pat. No. 5,569,234 issued to Buell et al. on Oct. 29, 1996, U.S. Pat. No. 4,940,464 issued to Van Gompel et al. on Jul. 10, 1990, and U.S. Pat. No. 5,092,861 issued to Nomura et al. on Mar. 3, 1992, the disclosures of each of which are hereby incorporated by reference.

Another disposable absorbent article for use in the present invention is an incontinence article. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. Pat. No. 5,304,161 issued to Noel, et al. on Apr. 19, 1994. The disclosures of each of these references are hereby incorporated by reference.

Another disposable absorbent article for use in the present invention is a feminine hygiene article, such as a sanitary napkin. Suitable feminine hygiene articles are disclosed in U.S. Pat. No. 4,556,146 issued to Swanson et al. on Dec. 3, 1985; U.S. Pat. No. 4,589,876 issued to Van Tilberg on Apr. 27, 1993; U.S. Pat. No. 4,687,478 issued to Van Tilburg on Aug. 18, 1997; U.S. Pat. No. 4,950,264 issued to Osborn, III on Aug. 21, 1990; U.S. Pat. No. 5,009,653 issued to Osborn, III on Apr. 23, 1991; U.S. Pat. No. 5,267,992 issued to Van Tilburg on Dec. 7, 1993; U.S. Pat. No. 5,389,094 issued to Lavash et al. on Feb. 14, 1995; U.S. Pat. No. 5,413,568 issued to Roach et al. on May 9, 1995; U.S. Pat. No. 5,460,623 issued to Emenaker et al. on Oct. 24, 1995; U.S. Pat. No. 5,489,283 issued to Van Tilburg on Feb. 6, 1996; U.S. Pat. No. 5,569,231 issued to Emenaker et al. on Oct. 29, 1996; and U.S. Pat. No. 5,620,430 issued to Bamber on Apr. 15, 1997, the disclosures of each of which are hereby incorporated by reference.

V. Protease Inhibition Methods

Standard in vitro assays for enzyme activity and inhibition of enzyme activity are well known. The reagents used to conduct these tests are generally commercially available. In general, a simple system comprises an enzyme-specific substrate which, when hydrolyzed by the enzyme, produces a colored product. The activity of the enzyme is measured spectrophotometrically as the degree of development of the colored product (i.e. the rate of color change) over a predetermined time period. Inhibition of enzyme activity is exhibited as a measurable decrease in the rate of color change over the same time period in the presence of an inhibitor.

For the Purified Protease assay and the Fecal Protease assays described below, the $IC_{50}$ for each inhibitor tested is calculated according to the following equation:

$$IC_{50} = [I]/[(v/v_i) - 1]$$

where: [I] is the inhibitor concentration tested, v is the rate of substrate cleavage in the absence of inhibitor and $v_i$ is the rate of substrate cleavage in the presence of inhibitor.

The following Purified Protease and Fecal Protease Methods are utilized to determine the inhibitory activity of putative protease inhibitors against a) purified proteases known to exist in feces; and b) the protease activity of feces itself; respectively. Any substance that meets the $IC_{50}$ criteria described above for inhibitory activity in any one of the following Methods is considered a protease inhibitor as defined herein. In the Methods, v and $v_i$ are measured as the change in absorbance (optical density, OD) at a given wavelength/time (e.g., minutes).

A. Purified Protease Methods

1. Purified Trypsin

To test the efficacy of protease inhibitors against purified trypsin, 0.05 mL of a putative inhibitor and 0.125 mL of 32 nM trypsin (e.g., Sigma, St. Louis, Mo., catalogue number T6424) in trypsin buffer (50 mM TRIS, 20 mM $CaCl_2$, pH 8.2) are added to a microcuvette. The cuvette is incubated at 25° C. for 10 minutes. To this mixture, 0.025 mL of substrate (4 mM Cbz-arginine-p-nitroanilide, e.g., Sigma, St. Louis, Mo., cat. no. C4893) in trypsin buffer is added to the cuvette, mixed, and the absorbance at 405 nm measured over 10 minutes at 25° C. The rate of substrate cleavage in the presence of inhibitor ($v_i$) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, $v_i$ and v, and the inhibitor concentration [α] are used to calculate $IC_{50}$ according to the equation expressed above.

2. Purified Chymotrypsin

To test the efficacy of protease inhibitors against purified chymotrypsin, 0.05 mL of a putative inhibitor and 0.125 mL of 16 nM chymotrypsin (e.g., Sigma, St. Louis, Mo., catalogue no. C8946) in chymotrypsin buffer (50 mM TRIS, 10 mM $CaCl_2$, pH 7.6) are added to a microcuvette. The cuvette is incubated at 25° C. for 10 minutes. To this mixture, 0.025 mL of substrate (0.6 mM N-Succ-Ala-Ala-Pro-Phe-p-nitroanilide, e.g., Sigma cat. no. S7388) in chymotrypsin buffer is added to the cuvette, mixed, and the absorbance at 405 nm measured over 10 minutes at 25° C. The rate of substrate cleavage in the presence of inhibitor ($v_i$) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, $v_i$ and v, and the inhibitor concentration [α] are used to calculate $IC_{50}$ according to the equation expressed above.

3. Purified Leucine Aminopeptidase

To test the efficacy of protease inhibitors against purified leucine aminopeptidase (LAP), 0.05 mL of a putative inhibitor and 0.125 mL of 0.06 U/mL LAP (e.g., Sigma, St. Louis, Mo., catalogue no. L5006) in LAP buffer (50 mM sodium phosphate, pH 7.2) are added to a microcuvette. The cuvette is incubated at 25° C. for 10 minutes. To this mixture, 0.025 mL of substrate (2.4 mM L-Leucine-p-nitroaniline, e.g., Sigma, St. Louis, Mo., cat. no. L9125) in LAP buffer is added to the cuvette, mixed, and the absorbance at 405 nm measured over 10 minutes at 25° C. The rate of substrate cleavage in the presence of inhibitor ($v_i$) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, $v_i$ and v, and the inhibitor concentration [α] are used to calculate $IC_{50}$ according to the equation expressed above.

B. Specific Fecal Protease Methods

The following is a general description of a method for obtaining a sample of feces suitable for use in Fecal Protease Methods.

For purposes of establishing a positive control to ensure that the pooled sample feces exhibit the requisite enzyme activity for assessing protease inhibitory activity, the following procedure is followed for each of the Fecal Protease Methods. Pooled infant feces (at least five different samples) are collected in a manner to keep them free of urine and contamination and mixed with water to obtain a weight by weight (w/w) mixture (e.g., 1:50 w/w). This mixture is then mixed thoroughly to obtain a homogeneous suspension by homogenization or sonication. The pooled fecal suspension is used as a source of protease activity as described below and will exhibit a rate of substrate turnover in the absence of inhibitor in the range of 0.005 $OD_{405}$ per minute to 0.020 $OD_{405}$ per minute. (Also, to ensure complete linearity the final absorbance should never exceed 1.5 $OD_{405}$ units). If the activity of the pooled infant feces is outside this range, it is not possible to accurately determine $IC_{50}$ values for putative protease inhibitors. However, the range of enzyme activity may be adjusted by increasing or decreasing the dilution factor accordingly for each enzyme. If this is not possible, a different group of subjects should be used to obtain the sample pool.

1. Fecal Trypsin Activity

To test the efficacy of protease inhibitors against the trypsin activity in feces, inhibitor and trypsin buffer (50 mM TRIS, 20 mM $CaCl_2$, pH 8.2) are added in a cuvette to obtain a final volume of 0.8 mL. To this mixture, 0.1 mL of substrate (3 mM Cbz-arginine-p-nitroanilide) is added to the cuvette. The cuvette is mixed by inversion and incubated at 25° C. for 5 minutes. A volume of 0.1 mL of fecal suspension is added to the cuvette, mixed and the absorbance at 405 nm minus the absorbance at 490 nm are measured over 5 minutes at 25° C. (The absorbance at 490 nm is a correction factor for the background absorbance due to the particulate fecal material, i.e., "interference"). The rate of substrate cleavage in the presence of inhibitor ($v_i$) is the slope of a plot relating the excess absorbance (i.e., the absorbance at 405 nm minus the absorbance at 490 nm) versus time. The same procedure is repeated without the putative inhibitor. The rate of substrate cleavage in the absence of inhibitor (v) is the slope of a plot relating the excess absorbance versus time. The rates, $v_i$ and v, and the inhibitor concentration [α] are used to calculate $IC_{50}$ according to the equation expressed above.

2. Fecal Chymotrypsin Activity

To test the efficacy of protease inhibitors against chymotrypsin activity in feces, inhibitor and chymotrypsin buffer (50 mM TRIS, 10 mM $CaCl_2$, pH 7.6) are added in a cuvette to obtain a final volume of 0.92 mL. To this mixture, 0.04 mL of substrate (1.25 mM N-Succ-Ala-Ala-Pro-Phe-p-nitroanilide) is added to the cuvette. The cuvette is mixed by inversion and incubated at 25° C. for 5 minutes. A volume of 0.04 mL of fecal suspension is added to the cuvette, mixed and the absorbance at 405 nm minus the absorbance at 490 nm measured over 5 minutes at 25° C. The rate of substrate cleavage in the presence of inhibitor ($v_i$) is the slope of a plot relating the excess absorbance (i.e., the absorbance at 405 nm minus the absorbance at 490 nm) versus time. The same procedure is repeated without the putative inhibitor. The rate of substrate cleavage in the absence of inhibitor (v) is the slope of a plot relating the excess absorbance versus time. The rates, $v_i$ and v, and the inhibitor concentration [α] are used to calculate $IC_{50}$ according to the equation expressed above.

3. Fecal LAP Activity

To test the efficacy of protease inhibitors against LAP activity in feces, inhibitor and LAP buffer (50 mM sodium phosphate, pH 7.2) are added in a cuvette to obtain a final volume of 0.95 mL. To this mixture, 0.03 mL of substrate (6 mM L-Leucine-p-nitroanilide) is added to the cuvette. The cuvette is mixed by inversion and incubated at 25° C. for 5 minutes. A volume of 0.02 mL of fecal suspension is added to the cuvette, mixed and the absorbance at 405 nm minus the absorbance at 490 nm measured over 5 minutes at 25° C. The rate of substrate cleavage in the presence of inhibitor ($v_i$) is the slope of a plot relating the excess absorbance (i.e., the absorbance at 405 nm minus the absorbance at 490 nm) versus time. The same procedure is repeated without the putative inhibitor. The rate of substrate cleavage in the absence of inhibitor (v) is the slope of a plot relating the excess absorbance versus time. The rates, $v_i$ and v, and the inhibitor concentration [I] are used to calculate $IC_{50}$ according to the equation expressed above.

Using the Purified Protease and Fecal Protease assays described above, the protease inhibitory activity of exemplary protease inhibitors employed in the absorbent articles of the invention was tested and the results of the testing are illustrated in Table 1.

TABLE 1

| | $IC_{50}$ Values (μM) | | | | | |
|---|---|---|---|---|---|---|
| | Purified Proteases | | | Specific Fecal Proteases | | |
| | Trypsin | Chymotrypsin | LAP* | Trypsin | Chymotrypsin | LAP* |
| Inhibitor | | | | | | |
| Soybean trypsin inhibitor | 0.25 | 0.026 | >10 | <0.01 | 0.06 | >20 |
| Aprotinin | 0.168 | 1 | >20 | 0.01 | 0.22 | >20 |
| Hexamidine diisethionate | 2.5 | >1000 | 256 | 2.3 | >1000 | 130 |
| p-Aminobenzamidine | 13.8 | >500 | >500 | 20 | >500 | >500 |
| Leupeptin | 0.14 | >500 | >500 | 0.11 | >500 | >500 |
| Pepstatin A | 324 | 4.9 | >500 | >500 | 300 | >500 |
| Chymostatin | >500 | <0.12 | >500 | >500 | 0.02 | >500 |

*LAP = leucine aminopeptidase

As illustrated in Table 1, each of the exemplary inhibitors exhibits an acceptable $IC_{50}$ for inhibition of at least one of the proteases tested by the Purified Protease and/or the Specific Fecal Protease Methods employed.

C. General Fecal Protease Methods

The general method described above for obtaining a sample of feces suitable for use in Fecal Protease Methods can be easily adapted by one skilled in the art to obtain appropriate samples of feces suitable for use in the General Fecal Protease Method listed below without undue experimentation.

To test the efficacy of protease inhibitors against the protease activity in feces, 50 μL of inhibitor and 50 μL of fecal suspension are added to a 1.5 mL microcentrifuge tube. The microcentrifuge tube is mixed by inversion and incubated at 25° C. for 45 minutes. Then, 50 µL of protease buffer (200 mM TRIS buffer containing 20 mM $CaCl_2$, pH 7.8) is added to the microcentrifuge tube. The microcentrifuge tube is again mixed by inversion and incubated at 25° C. for 45 minutes. Then, 50 µL of protease substrate (0.4% casein-resorufin, e.g., Boehringer Mannheim, Indianapolis, Ind., catalogue no. 1,734,334) is added to the microcentrifuge tube. The microcentrifuge tube is again mixed by inversion and incubated at 37° C. for 60 minutes for the substrate cleavage reaction to take place. Then, 480 µL of trichloroacetic acid (5% w/v) is added to stop the reaction and precipitate any unreacted casein-resorufin. The microcentrifuge tube is mixed by inversion incubated at 37° C. for 15 minutes. The microcentrifuge tube is spun at a relative centrifugal force (RCF) of 20,800 times gravity for 5 min. Then, 400 µL of the supernatant is added to 600 µL of assay buffer (0.5 M TRIS, pH 8.8) in a cuvette. The cuvette is mixed by inversion and the absorbance at 574 nm are measured. The same procedure is repeated without the putative inhibitor. A is the absorbance at 574 nm in the absence of the inhibitor. $A_i$ is the absorbance at 574 nm in the presence of the inhibitor. Before the start of the reaction, A and $A_i$ are nearly zero. Therefore, the rate of substrate cleavage in the presence of inhibitor ($v_i$) can be calculated by dividing the absorbance at 574 nm ($A_i$) over reaction time. The rate of substrate cleavage in the absence of inhibitor (v) can be calculated by dividing the absorbance at 574 nm (A) over reaction time. The rates, $v_i$ and v, and the inhibitor concentration [I] are used to calculate $IC_{50}$ according to the equation expressed above.

TABLE 2

| Inhibitor | $IC_{50}$ VALUES (µM)<br>General Fecal Proteases |
|---|---|
| Soybean trypsin inhibitor | 4.9 |
| Hexamidine | 31 |
| Leupetin | >320 |
| Pepstatin A | >32 |
| Chymostatin | 64 |
| 4-(2-aminoethyl)-benzenesulfonylfluoride hydrochloride | 217 |

D. Absorbent Article Test Method

To determine the presence of a protease inhibitor in any portion of an absorbent article (e.g., topsheet, absorbent core, backsheet and/or additional layers, leg cuffs, fasteners, side panels, inserted elements, or any combination of these), a small sample of the article is obtained from the desired portion and an extraction of the inhibitor is carried out. As is known to one skilled in the art, a water soluble inhibitor would be extracted with water or a water-based solvent, whereas a lipid-soluble inhibitor would be extracted with a lipid-based solvent. The following description is only of an exemplary method for determining the presence of a protease (trypsin) inhibitor in the article and is not intended to be limiting, as the method may be employed to test for the presence of inhibitors of other proteases, and other different methods may be devised by one skilled in the art without undue experimentation.

In a method for testing a topsheet of an article for a trypsin inhibitor, random ¾ inch punches are made in the core area of the diaper. The topsheet is removed from the punch and placed in a 1.5 mL centrifuge vial. The sample is soaked overnight in 0.75 mL water or other extracting solvent such as the 50 mM TRIS, 20 mM $CaCl_2$, pH 8.2 buffer described above. An aliquot (0.125 mL) of the supernatant liquid is removed and added to a cuvette containing 0.025 mL of freshly prepared 160 nM human pancreatic trypsin in TRIS-HCl containing 20 mM $CaCl_2$, pH 8.2 and incubated for 10 minutes at 25° C. A control sample containing buffer only is similarly prepared in a second cuvette. Cbz-arginine-p-nitroanilide substrate (0.025 mL of a 4 mM solution) is added to each cuvette and the test and control samples are incubated for 5 minutes. The change in absorbance at 405 nm for each sample is then monitored over 10 minutes. The skilled artisan will recognize that the protocol can be used to assay for protease inhibitory activity in other article components, such as the absorbent core and the like.

The absorbent article is considered to demonstrate protease inhibitory activity if the sample extract demonstrates at least a 10% reduction, preferably at least a 20% reduction, more preferably at least a 50% reduction, and most preferably at least an 80% reduction in substrate hydrolysis by a protease compared to the control, buffer only, sample, as measured by the Absorbent Article Test Method. Typically the reduction in substrate hydrolysis will be about 10% to about 99%, more typically about 20% to about 99%, still more typically about 50% to about 99%, and most typically about 80% to about 99%.

The absorbent article is also considered to demonstrate protease inhibitory activity if the sample contains any protease inhibiting substance, such as any of the previously described protease inhibitors as well as substances that do not necessarily meet the $IC_{50}$ criteria for protease inhibitory activity described above, when measured by either the Purified Protease or the Fecal Protease Methods, e.g., substances such as L-1-chloro-3-[4-tosylamido]-7-amino-2-heptanone-HCl (TLCK), L-1-chloro-3-[4-tosylamido]-4-phenyl-2-butanone (TPCK), tranexamic acid, and the like.

E. In Vitro Skin Test for Inhibition of IL-1α Production

In an in vitro method to determine the efficacy of protease inhibitors in preventing the proinflammatory response of the skin to feces and fecal enzymes, human keratinocytes are obtained from epidermal tissue and cultured in serum free medium in plastic culture vessels containing a nylon mesh surface for a period of time until they are confluent. The mesh surface is then raised to the liquid air interface in order to promote differentiation and formation of multilayered organized layers analogous to those found in vivo, including a well defined stratum corneum barrier layer. Any cell culture system that promotes the growth and differentiation of keratinocytes, as described, may be employed. A commercially available cell culture system suitable for use in the invention is Epiderm (MatTek Corporation, Ashland, Mass.).

Infant feces are collected in a manner to keep them free of urine contamination and diluted with phosphate-buffered saline (PBS) (pH 7.2-7.4.) The mixture is then mixed thoroughly to obtain a homogeneous suspension by homogenization or sonication. To assay for IL-1α production due to fecal enzyme activity, an aliquot of the homogenate is diluted with PBS and added to the surface of a control culture in a culture vessel. To assay for inhibition of IL-1α production due to protease activity, a predetermined quantity of a putative protease inhibitor is added to an otherwise identical diluted aliquot of the homogenate prior to adding it to the surface of a test culture. The cultures are allowed to incubate in a controlled atmosphere. At selected times, the control cultures and inhibitor-treated test cultures, and the underlying culture media are harvested. The culture media are assayed for the presence of IL-1α by known methods. For example, a suitable assay for IL-1α is an enzyme-linked immunoabsorbent method commercially available as Quantikine from R&D Systems, Minneapolis, Minn.

The percent reduction in IL-1α production due to the presence of the protease inhibitor is calculated as follows:

$$\% \text{ reduction} = \frac{IL\text{-}1\alpha \text{ from control cultures minus } IL\text{-}1\alpha \text{ from test cultures}}{IL\text{-}1\alpha \text{ from control cultures}} \times 100\%$$

Using this standard assay, the ability of exemplary serine protease inhibitors, soybean trypsin inhibitor and hexamidine diisethionate ("hexamidine"), to inhibit IL-1α production by cultured keratinocytes in the presence of feces was tested. The results showed that hexamidine, at concentration of 1000 μM and 100 μM, reduced IL-1α production from skin cultures treated with feces by 51-88% and 5%, respectively. A concentration of 10 μM soybean trypsin inhibitor was sufficient to reduce IL-1α production by 56-75%. Heat treatment (90° C.) of the feces prior to testing for IL-1α production led to a near complete elimination of IL-1α production, suggesting that the principal agent or agents involved in the evoking the cytokine response are denaturable proteins. The results indicate that inhibitors of the serine protease trypsin (see Table 1) were also effective in reducing IL-1α production from skin cell cultures.

VI. Incorporation of Inhibitors into Absorbent Articles

1. Vehicle

The protease inhibitor for use in the absorbent article of the invention may be water-soluble or lipid-soluble and may be incorporated into the absorbent article neat, such as in dry powder or particulate form, or in the form of a solution, suspension, dispersion, emulsion or the like in a pharmaceutically and dermatologically acceptable carrier vehicle that does not interfere with the protease inhibitory activity of the compound. The inhibitor may also be incorporated in another structure that in turn is incorporated into the article during manufacture or assembly. For example, the inhibitor may be coated onto or otherwise attached or bound to a nanophase particulate structure or other solid support such as glass, plastic or agarose beads, and the like, or contained in pressure-rupturable or dissolvable microcapsules and the like, or contained in an absorbent material. The use of other types of incorporatable elements for containing the inhibitor and methods for their incorporation will be readily apparent to one skilled in the art.

Carrier vehicles for the inhibitor include compositions that are in the form of lotions, creams, oils, ointments, powders, foams, or gels and the like and that may contain any ingredients commonly used in the art for such compositions. The ingredients of the compositions will depend on the character of the composition; thus, for example, lotions will generally comprise different ingredients than powders. Compositions that are cosmetic in nature may further comprise a wide variety of optional ingredients such as non-occlusive moisturizers, humectants, gelling agents, neutralizing agents, perfumes, coloring agents, and the like. Other ingredients, such as surfactants and the like, that may be present in the composition are described more fully below under "Skin Care Compositions". It is preferable that protease inhibitor-containing compositions intended for transfer to the skin have a pH of no less than about 4 and no greater than about 7.5.

2. Incorporation

The protease inhibitor employed in the absorbent articles of the invention is incorporated into the article in a configuration that does not itself interfere with the normal function of the various structures of the article (e.g., the absorbency of the core, the liquid perviousness of the top sheet, and the like). The inhibitor may be incorporated into any portion or portions of the article including, but not limited to, the topsheet, the backsheet, the absorbent core, any secondary layer(s) intermediate the core and sheet layers, a leg cuff, a side panel, a waist region, a fastener, an insertable element such as an absorbent material inserted into the absorbent article for use during wear of the article, specialized structures such as those employed to contain bowel movements (e.g., bowel movement "pockets"), and the like. The inhibitor may be incorporated into the article neat or, alternatively, the inhibitor may be contained in a delivery system described further below that is incorporated into any of the foregoing portions of the article and that delivers the protease inhibitor directly or indirectly to the skin of a wearer during normal wear of the article.

Any number of different protease inhibitors or mixtures of protease inhibitors, whether or not they are incorporated into a delivery system, may be uniformly or nonuniformly distributed throughout the absorbent article. The absorbent article preferably contains the protease inhibitor at such a level that the inhibitor or a mixture of inhibitors comprises from 0.0001% to 30%, more preferably from 0.0001% to 10%, still more preferably from 0.001% to 5%, and especially 0.001% to 1% by weight of the article.

The protease inhibitor may be incorporated directly onto the surface of or within the structure of any type of topsheet, including woven, nonwoven and apertured structured topsheets, the backsheet, and/or absorbent core materials, or other components of the article during manufacture or assembly by diverse methods which will be readily apparent to those skilled in the art. For example the inhibitor can be applied, optionally after being dispersed in a liquid or semi-solid carrier vehicle, to the topsheet, to the absorbent core, or to the core side of the backsheet, by spraying, dipping, printing, soaking or otherwise contacting the selected structural element with the inhibitor and optionally its carrier vehicle. Among the many other techniques that can be employed are graft or radical polymerization, or steam treating of the structural elements in order to bind the inhibitor by hydrogen bonding that is easily reversed when such surfaces are wetted by body waste to release the inhibitor.

Preferably, the inhibitor is incorporated into at least a portion of a wearer-contacting surface of the article and is available for automatic transfer to the wearer's skin during normal contact, wearer motion and/or body heat during wear of the article. Alternatively, the article further comprises a delivery system that contains the protease inhibitor and, during wear of the article the delivery system automatically delivers at least a portion of the inhibitor to the skin of the wearer. In each of these embodiments of the invention the protease inhibitor is transferred to the skin, preferably before a bowel movement occurs, for availability to act at the skin/feces interface after a bowel movement. In a more preferred embodiment, the delivery system is a skin care composition containing the protease inhibitor and various emollients and immobilizing agents, as described further below, that is delivered directly from a wearer-contacting surface to the wearer's skin to perform a barrier function to feces as well as a fecal protease inhibiting function. Most preferably, the use or preferably the repeated use of articles in which the protease inhibitor is transferred or delivered directly or indirectly to the wearer's skin provides an accumulation of the protease inhibitor for more effective prevention or reduction of inflammation of the skin due to contact with fecal proteases.

In another embodiment of the invention, the protease inhibitor is positioned in the absorbent article neat or in a delivery system in such a manner and location that it is available to inactivate proteases in feces, especially runny feces, deposited in the article before transfer of feces to the skin of the wearer.

In another embodiment of the invention, the protease inhibitor is positioned within the absorbent article such that it is available to reduce or eliminate fecal protease activity in fecal fluids, or urine contaminated with feces, that may penetrate into the absorbent interior of the article and that may, for any reason, later come in contact with a wearer-contacting surface. Again, the protease inhibitor may be initially available or may be contained in a delivery system within the article.

VII. Delivery Systems

Protease inhibitors, or compositions containing them, may be releasably incorporated into any delivery system known to those skilled in the art that directly or indirectly facilitates the transfer of the protease inhibitor to the skin of the wearer of the article to protect against irritation due to fecal proteases at the skin-feces interface. The delivery system may contain the protease inhibitor neat, as a powder or particulate, or in a solution, suspension, dispersion, emulsion, or the like in a carrier vehicle or skin care composition. When released from the delivery system the protease inhibitor is freed to migrate from the location of the delivery system in the article to a wearer-contacting surface to the skin of the wearer. The delivery system may be a component of any portion or portions of the absorbent article including, but not limited to, the topsheet, the backsheet, the absorbent core, any secondary layer(s) intermediate the core and sheet layers, a leg cuff, a side panel, a waist region, a fastener, an insertable element such as an absorbent material inserted into the absorbent article for use during wear of the article, specialized structures such as those employed to contain bowel movements (e.g., bowel movement "pockets"), and the like. Preferably the delivery system is positioned in proximity to the wearer's skin and, more preferably is a component of a wearer-contacting surface of portions of the article such as the topsheet, side panels, leg cuffs, waist region, fasteners and the like. Most preferably the delivery system is a skin care composition described further below that is incorporated into the topsheet.

The delivery system may contain and/or deliver the protease inhibitor in any form such as those described above, including powder, flake or particulate form, or in the form of a solution, suspension, dispersion, emulsion or the like in a pharmaceutically and dermatologically acceptable carrier vehicle. When the inhibitor is released by the delivery system it may be in an active functional form such as in a solution, suspension, emulsion or the like, or it may be non-functional such as in powder or particulate form and activatable by contact with moisture from urine and feces or other known means.

The types of delivery systems that are useful in the absorbent articles of the invention for facilitating automatic transfer of the protease inhibitor from any portion of the article to the skin of a wearer will be readily apparent to those skilled in the art. Exemplary delivery systems include, for example, pressure-rupturable or dissolvable microcapsules that are induced to express the inhibitor or inhibitor composition upon dissolving due to contact with moisture from urine or feces, or rupturing due to pressure from the body or manual rupturing by a user prior to applying the article to a wearer. For example, a water-soluble film that encloses and expresses a powder upon contact with moisture is described in U.S. Pat. No. 4,790,836 and would be a suitable material for use in microcapsules containing the protease inhibitor in any form such as a powder, particulate, liquid or semi-solid. Examples of pressure-rupturable microcapsules suitable for containing the protease inhibitor are described in U.S. Pat. No. 3,585, 998. Such microcapsules may be present in any portion of the absorbent article, including the topsheet. U.S. Pat. No. 4,623, 339 describes an insertable layer that is removable from an absorbent article prior to use and manually pressure activatable to express a substance through slits in the layer. The disclosures of each of the foregoing patents are hereby incorporated by reference.

Other suitable delivery systems for containing the inhibitors or inhibitor composition include, but are not limited to, "cells" in the article that are enclosed or partially enclosed voids, regularly or irregularly shaped, that release the inhibitor when in contact with moisture, heat or pressure; and water-soluble adhesives and other such compositions which release the inhibitor upon contact with moisture, and the like.

Regardless of the delivery system employed, the protease inhibitor or protease inhibitor-containing composition upon release may be migratable from its original location, e.g., it may be moved by the flow of urine, by motion of the wearer, by pressure and the like, or because of a decrease in viscosity upon exposure to body heat, to other regions in the absorbent article. Protease inhibitors that are hydrophilic or are incorporated into vehicles that are hydrophilic may migrate throughout hydrophilic structures of the absorbent article, such as through hydrophilic pores or other openings that allow urine to flow from the topsheet to the core. Preferably, however, the delivery systems containing protease inhibitors, or compositions comprising the inhibitors are positioned in proximity to the skin of the wearer. In a preferred embodiment, the protease inhibitors are dissolved, suspended or emulsified components of skin care compositions that can be positioned anywhere in the article, but preferably are incorporated into a wearer-contacting surface of the absorbent article such as the topsheet, side panel, waist region, leg cuff, fastening device and the like.

Suitable skin care compositions for delivering the protease inhibitor are described further below. In either of these preferred embodiments, the skin care composition preferably comprises about 0.01% to about 50%, more preferably about 0.5% to about 25%, and especially about 1% to about 10% by weight of the protease inhibitor.

VIII. Skin Care Compositions

Skin care compositions suitable for use in the preferred embodiments of the invention are described in U.S. patent application Ser. Nos. 08/926,532 and 08/926,533, each filed on Sep. 10, 1997; U.S. Pat. No. 5,607,760 issued Mar. 4, 1997; U.S. Pat. No. 5,609,587 issued Mar. 11, 1997; U.S. Pat. No. 5,635,191 issued Jun. 3, 1997; and U.S. Pat. No. 5,643, 588 issued Jul. 1, 1997, the disclosures of each of which are hereby incorporated by reference.

In addition to its function as a vehicle for delivering an effective concentration of a protease inhibitor to a wearer's skin, the skin care composition that contains the protease inhibitor may also comprise ingredients that, for example, reduce the adherence of feces to skin (e.g., to improve the ease of bowel movement clean up), provide a skin/feces barrier function (e.g., to coat the skin to prevent the adherence of feces) while remaining relatively liquid impervious but vapor pervious), or provide other therapeutic benefits to the skin (e.g., improve skin softness, maintain or improve skin health), and the like. The skin care composition may be in a variety of forms, including, but not limited to, emulsions, lotions, creams, ointments, salves, powders, suspensions, encapsulations, gels, and the like.

In order to deliver an effective concentration of the protease inhibitor to the skin via an absorbent article over time, an effective amount of the skin care composition containing the inhibitor that is applied to or migrated to one or more of the wearer-contacting surfaces of the article depends, to a large extent on the particular skin care composition used. The quantity of the composition on at least a portion of the wearer-contacting surface of the absorbent article preferably ranges from about 0.05 mg/in$^2$ (0.0078 mg/cm$^2$) to about 80 mg/in$^2$ (12 mg/cm) more preferably from about 1 mg/in$^2$ (0.16 mg/cm$^2$) to about 40 mg/in$^2$ (6 mg/cm$^2$), still more preferably from about 4 mg/in$^2$ (0.6 mg/cm$^2$) to about 26 mg/in$^2$ (4 mg/cm$^2$). However, these ranges are by way of illustration only and the skilled artisan will recognize that the nature of the composition will dictate the level that must be applied to deliver an effective amount of the protease inhibitor and that the desirable level is ascertainable by routine experimentation in light of the present disclosure.

While the amount of skin care composition applied to the absorbent article is an important aspect of the present invention, more important is the amount of composition transferred to the wearer's skin during use of one or more treated articles. Though the amount of the protease inhibitor-containing composition delivered to the skin will depend to some degree on the nature of the composition employed, relatively low amounts may be delivered while still providing a minimum inhibitory concentration of the protease inhibitor to the skin. This is particularly true for preferred compositions, such as that described in Example 1.

To determine the amount of protease inhibitor transferred to a wearer's skin after wearing one or more treated articles, a method is provided below for determining the amount of skin care composition transferred to the skin. With regard to the level of skin care composition that is transferred to the wearer during use of one treated absorbent article worn for a period of about 3 hours (a typical daytime wear time), particularly for preferred skin care compositions such as that described in Example 1, preferred is where at least about 0.01 mg/in$^2$ (0.0016 mg/cm$^2$), more preferably at least about 0.05 mg/in$^2$ (0.0078 mg/cm$^2$), still more preferably at least about 0.1 mg/in$^2$ (0.016 mg/cm$^2$), of the composition is transferred to the skin over a three hour wear period. Typically, the amount of composition delivered by one treated article will be from about 0.01 mg/in 2 (0.0016 mg/cm$^2$) to about 5 mg/in$^2$ (0.78 mg/cm$^2$), more preferably from about 0.05 mg/in$^2$ (0.0078 mg/cm$^2$) to about 3 mg/in$^2$ (0.47 mg/cm$^2$), still more preferably from about 0.1 mg/in$^2$ (0.016 mg/cm$^2$) to about 2 mg/in$^2$ (0.31 mg/cm$^2$), over a three hour wear period.

For continual use of treated articles (in other words, changes occur in accordance with normal use patterns, which typically include changes every 3 to 4 hours during the day and a fresh article before overnight sleep) such as for a period of 24 hours, it will be preferred that at least about 0.03 mg/in$^2$ (0.0047 mg/cm$^2$), more preferably at least about 0.1 mg/in$^2$ (0.016 mg/cm$^2$), still more preferably at least about 0.3 mg/in$^2$ (0.047 mg/cm$^2$), of the composition is transferred to the wearer's skin over the 24 hour period. Typically, the amount of composition delivered after a period of 24 hours where treated articles are applied at each change, will be from about 0.03 mg/in$^2$ (0.0047 mg/cm$^2$) to about 18 mg/in$^2$ (2.79 mg/cm$^2$), more typically from about 0.1 mg/in$^2$ (0.016 mg/cm$^2$) to about 10 mg/in$^2$ (1.55 mg/cm$^2$), still more typically from about 0.3 mg/in$^2$ (0.047 mg/cm$^2$) to about 6 mg/in$^2$ (0.93 mg/cm$^2$).

It will be recognized that of the numerous materials useful in the protease inhibitor-containing skin care compositions delivered to skin in accordance with the invention, those that have been deemed safe and effective skin care agents are logical materials for use herein. Such materials include Category I actives as defined by the U.S. Food and Drug Administration's (FDA) Tentative Final Monograph on Skin Protectant Drug Products for Over-the-Counter Human Use (21 C.F.R. §347), which presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Food and Drug Administration's Tentative Final Monograph on Skin Protectant Drug Products for Over-the-Counter Human Use (21 C.F.R. §347), which presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like.

Many of the FDA monographed skin care ingredients are currently utilized in commercially available skin care products, such as A and D Ointment, Vaseline Petroleum Jelly, Desitin Diaper Rash Ointment and Daily Care ointment, Gold Bond Medicated Baby Powder, Aquaphor Healing Ointment, Baby Magic Baby Lotion, Johnson's Ultra Sensitive Baby Cream. An effective concentration of a protease inhibitor may be incorporated into any of these commercial products or other commercially available skin care products not here listed and applied to absorbent articles to create treated articles for use in the present invention.

As discussed further hereinafter, the skin care compositions useful for transferring protease inhibitors to the skin of the wearer preferably, though not necessarily, have a melting profile such that they are relatively immobile and localized on the wearer-contacting surface of the article at room temperature, are readily transferable to the wearer at body temperature, and yet are not completely liquid under extreme storage conditions. Preferably, the compositions are easily transferable to the skin by way of normal contact, wearer motion, and/or body heat. Because the composition preferably is substantially immobilized on the article's wearer-contacting surface, relatively low levels of composition are needed to impart the desired skin care benefits. In addition, special barrier or wrapping materials may be unnecessary in packaging the treated articles useful in the methods of the present invention.

In a preferred embodiment, the skin care compositions useful herein are water-in-oil emulsions, wherein the protease inhibitor is in solution or suspension in either the aqueous phase or the oil phase. However, the skin care composition itself may be solid or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes a liquid component. Preferably, the protease inhibitor-containing compositions of the present invention have a zero shear viscosity between about $1.0 \times 10^6$ centipoise and about $1.0 \times 10^8$. More preferably, the zero shear viscosity is between about $5.0 \times 10^6$ centipoise and about $5.0 \times 10^7$ centipoise. As used herein the term "zero shear viscosity" refers to a viscosity measured at very low shear rates (e.g., $1.0 \, \text{sec}^{-1}$) using plate and cone viscometer (a suitable instrument is available from TA Instruments of New Castle, Del. as model number CSL 100). One of skill in the art will recognize means other than high melting point components (as discussed below) can be used to provide comparable viscosities measured for such compositions comprising such means can be measured by extrapolating a plot of viscosity vs. shear rate for such compositions to a shear rate of zero at a temperature of about 20° C.

Preferred compositions are at least semi-solid at room temperature to minimize composition migration before wear of the article. In addition, the compositions preferably have a final melting point (100% liquid) above potential "stressful" storage conditions that can be greater than 45° C. (e.g., warehouse in Arizona, car trunk in Florida, etc.). Representative compositions having these melt characteristics are described in detail in U.S. Pat. Nos. 5,643,588, 5,607,760, 5,609,587, and 5,635,191, the disclosure of each of which has been incorporated herein by reference. Specifically, preferred compositions will have the following melt profile:

| Characteristic | Preferred Range | Most Preferred |
|---|---|---|
| % liquid at room temp. (20° C.) | 2-50 | 3-25 |
| % liquid at body temp. (37° C.) | 25-95 | 30-90 |
| final melting point (° C.) | 38 | 45 |

By being solid or semisolid at ambient temperatures, preferred compositions containing the protease inhibitors do not have a tendency to flow and migrate to a significant degree to undesired locations of the article to which they are applied. This means less skin care composition is required for imparting desirable therapeutic, protective and/or conditioning benefits.

To enhance immobility of preferred compositions before wear of the article, the viscosity of the formulated compositions should be as high as possible to prevent flow within the article to undesired location. Unfortunately, in some instances, higher viscosities may inhibit transfer of composition to the wearer's skin. Therefore, a balance should be achieved so the viscosities are high enough to keep the compositions localized on the surface of the article, but not so high as to impede transfer to the wearer's skin. Suitable viscosities for the compositions will typically range from about 5 to about 500 centipoise, preferably from about 5 to about 300 centipoise, more preferably from about 5 to about 100 centipoise, measured at 60° C. using a rotational viscometer (a suitable viscometer is available from Lab Line Instruments, Inc. of Melrose Park, Ill. as Model 4537). The viscometer is operated at 60 rpm using a number 2 spindle.

For skin care compositions designed to provide a therapeutic and/or skin protective benefit in addition to the benefit derived from the protease inhibitor, a useful active ingredient in these compositions is one or more skin protectants or emollients. As used herein, the term "emollient" is a material that protects against wetness or irritation, softens, soothes, supples, coats, lubricates, moisturizes, protects and/or cleanses the skin. (It will be recognized that several of the monographed actives listed above are "emollients", as that term is used herein.) In a preferred embodiment, these emollients will have either a plastic or liquid consistency at ambient temperatures, i.e., 20° C.

Representative emollients useful in the present invention include, but are not limited to, emollients that are petroleum-based; sucrose ester fatty acids; polyethylene glycol and derivatives thereof, humectants; fatty acid ester type; alkyl ethoxylate type; fatty acid ester ethoxylates; fatty alcohol type; polysiloxane type; propylene glycol and derivatives thereof, glycerine and derivatives thereof, including glyceride, acetoglycerides, and ethoxylated glycerides of $C_{12}$-$C_{28}$ fatty acids; triethylene glycol and derivatives thereof, spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention.

Suitable fatty acid ester type emollients include those derived from $C_{12}$-$C_{28}$ fatty acids, preferably $C_{16}$-$C_{22}$ saturated fatty acids, and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$-$C_{28}$, preferably $C_{12}$-$C_{16}$) and shorter chain fatty acids e.g., lactic acid, such as lauryl lactate and cetyl lactate.

Suitable alkyl ethoxylate type emollients include $C_{12}$-$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$-$C_{22}$ fatty alcohols, preferably $C_{16}$-$C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

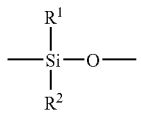

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Suitable fatty ester type emollients also include polyolpolyesters as described in U.S. Pat. No. 5,609,587, issued to Roe on Mar. 11, 1997, the disclosure of which is incorporated herein by reference. Exemplary polyols include, but are not limited to, polyhydric compounds such as pentaerythritol; sugars such as raffinose, maltodextrose, galactose, sucrose, glucose, xylose, fructose, maltose, lactose, mannose and erythrose; and sugar alcohols such as erythritol, xylitol, malitol, mannitol and sorbitol. Such polyols are esterified with fatty acids and/or other organic radicals having at least two carbon atoms and up to 30 carbon atoms. While it is not necessary that all of the hydroxyl groups of the polyol be esterified, preferred polyolpolyester emollients of the present invention have substantially all (e.g. at least about 85%) of the hydroxyl groups esterified. Particularly preferred are sucrose polyolpolyesters such as sucrose polycottonate, sucrose polysoyate, and sucrose polybehenate. Mixtures of such polyolpolyesters are also suitable emollients for the present invention.

Suitable humectants include glycerine, propylene glycol, sorbitol, trihydroxy stearin, and the like.

When present, the amount of emollient that can be included in the composition will depend on a variety of factors, including the particular emollient involved, the skin benefits desired, the other components in the composition and like factors. The composition will comprise from 0 to 100%, by total weight, of the emollient. Preferably, the composition will comprise from about 10 to about 95%, more preferably from about 20 to about 80%, and most preferably from about 40 to about 75%, by weight, of the emollient.

Another optional, preferred component of the protease inhibitor-containing skin compositions useful in the present invention is an agent capable of immobilizing the composition (including the protease inhibitor, the preferred emollient and/or other skin condition/protective agents) in the desired location in or on the treated article. Because certain of the preferred emollients in the composition have a plastic or liquid consistency at 20° C., they tend to flow or migrate, even when subjected to modest shear. When applied to a wearer-contacting surface or other location of an absorbent article, especially in a melted or molten state, the emollient will not remain primarily in or on the treated region. Instead, the emollient will tend to migrate and flow to undesired regions of the article.

Specifically, if the emollient migrates into the interior of the article, it can cause undesired effects on the absorbency of the article core due to the hydrophobic characteristics of many of the emollients and other skin conditioning agents used in the compositions useful in the methods of the present invention. It also means that much more emollient has to be applied to the article to get the desired therapeutic and/or protective benefits. Increasing the level of emollient not only increases the cost, but also exacerbates the undesirable effect on the absorbency of the article's core and undesired transfer of composition during processing/converting of the treated articles.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier), it entraps the emollient on the surface of the article's wearer contacting surface or in the region to which it is applied.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the article's wearer contacting surface or in the region to which it is applied.

It is also advantageous to "lock" the immobilizing agent on the wearer contacting surface or the region of the article to which it is applied. This can be accomplished by using immobilizing agents which quickly set up (i.e., solidify) upon application to the article. In addition, outside cooling of the treated article via blowers, fans, cold rolls, etc. can speed up crystallization of the immobilizing agent.

In addition to being miscible with (or solubilized in) the emollient, the immobilizing agent will preferably have a melting profile that will provide a composition that is solid or semisolid at ambient temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

When utilized, immobilizing agents useful herein can be selected from any of a number of agents, so long as the protease-inhibiting properties of the skin care composition provide the skin benefits described herein. Preferred immobilizing agents will comprise a member selected from the group consisting of $C_{14}$-$C_{22}$ fatty alcohols, $C_{12}$-$C_{22}$ fatty acids, and $C_{12}$-$C_{22}$ fatty alcohol ethoxylates having an average degree of ethoxylation ranging from 2 to about 30, and mixtures thereof. Preferred immobilizing agents include $C_{16}$-$C_{18}$ fatty alcohols, most preferably crystalline high melting materials selected from the group consisting of cetyl alcohol, stearyl alcohol, behenyl alcohol, and mixtures thereof. (The linear structure of these materials can speed up solidification on the treated absorbent article.) Mixtures of cetyl alcohol and stearyl alcohol are particularly preferred. Other preferred immobilizing agents include $C_{16}$-$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$-$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$-$C_{18}$ fatty alcohols increase the rate of crystallization of the composition causing the composition to crystallize rapidly onto the surface of the substrate.

Other types of immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin.

Suitable polyhydroxy fatty acid esters for use in the present invention will have the formula:

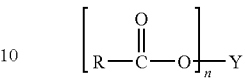

wherein R is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof, Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$-$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$-$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$-$C_{22}$ saturated fatty acid esters of sucrose. Sucrose monoesters and diesters are particularly preferred and include sucrose mono- and di-stearate and sucrose mono- and di-laurate.

Suitable polyhydroxy fatty acid amides for use in the present invention will have the formula:

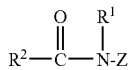

wherein $R^1$ is H, $C_1$-$C_4$ hydrocarbyl, 2-hydroxyethyl, 2-hydroxypropyl, methoxyethyl, methoxypropyl or a mixture thereof, preferably $C_1$-$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof, and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —CH($CH_2OH$)—[$(CHOH)_{n-1}$]—$CH_2OH$, —$CH_2OH$—$CH_2$—$(CHOH)_2$—$(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

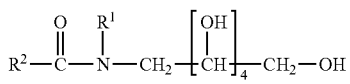

wherein $R^1$ is methyl or methoxypropyl; $R^2$ is a $C_{11}$-$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having hydrophilic lipophilic balance (HLB) values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the article. Additionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S. P. 434 from Strahl and Pitsch Inc. P.O. Box 1098 West Babylon, N.Y. 11704.

The amount of the optional immobilizing agent that can be included in the composition will depend on a variety of factors, including the actives (e.g., emollients) involved, the particular immobilizing agent involved, if any, the other components in the composition, whether an emulsifier is required to solubilize the immobilizing agent in the other components, and like factors. When present, the composition will typically comprise from about 5 to about 90% of the immobilizing agent. Preferably, the composition will comprise from about 5 to about 50%, most preferably from about 10 to about 40%, of the immobilizing agent.

It is highly desirable that at least a portion of the article's topsheet be made of a hydrophilic material to promote rapid transfer of liquids (e.g., urine) through the topsheet. Similarly, it may be desirable that the composition be sufficiently wettable to ensure that liquids will transfer through the topsheet rapidly. Alternatively, hydrophobic skin care compositions may be utilized, so long as they are applied such that the fluid handling properties of the topsheet are adequately maintained. (For example, as discussed below, nonuniform application of the composition to the topsheet is one means to accomplish this goal.) This diminishes the likelihood that body exudates will flow off the composition-treated topsheet rather than being drawn through the topsheet and being absorbed by the absorbent core. Where a hydrophilic composition is desired, depending upon the particular components used in the composition, a hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$-$C_{18}$ fatty alcohols having HLB values below about 7 may require addition of hydrophilic surfactant to improve wettability when the composition is applied to article topsheets. Similarly, a hydrophobic emollient such as petrolatum may require the addition of a hydrophilic surfactant if hydrophilic composition is desired. Of course, the concern around wettability is not a factor when the wearer-contacting surface under consideration is other than the article's topsheet or when fluid handling properties of the topsheet are adequately maintained via other means (e.g., nonuniform application).

Suitable hydrophilic surfactants will preferably be miscible with the other components of the skin care composition so as to form blended mixtures. Because of possible skin sensitivity of those using disposable absorbent products to which the composition is applied, these surfactants should also be relatively mild and non-irritating to the skin. Typically, these hydrophilic surfactants are nonionic to be not only non-irritating to the skin, but also to avoid other undesirable effects on any other structures within the treated article. For example, reductions in tissue laminate tensile strength, adhesive bond sufficiencies, and the like.

Suitable nonionic surfactants may be substantially nonmigratory after the composition is applied to the articles and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in compositions that will be applied to the articles, at least in the liquid discharge region of the diaper, include alkylglycosides; alkylglycoside ethers as described in U.S. Pat. No. 4,011,389 (Langdon, et al), issued Mar. 8, 1977, which is incorporated by reference; alkylpolyethoxylated esters such as Pegosperse 1000MS (available from Lonza, Inc., Fair Lawn, N.J.), ethoxylated sorbitan mono-, di- and/or tri-esters of $C_{12}$-$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$-$C_{15}$ linear alcohols with 9 moles of ethylene oxide), marketed by Union Carbide Corporation; KYRO EOB (condensation product of $C_{13}$-$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$-$C_{15}$ linear alcohols with 12 moles of ethylene oxide) and NEODOL 23-6.5T (condensation product of $C_{12}$-$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{1-8}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the composition includes Aerosol OT, a dioctyl ester of sodium sulfosuccinic acid marketed by American Cyanamid Company.

Still another type of suitable surfactant for use in the composition includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the composition.

Where a hydrophilic composition is desired, the amount of hydrophilic surfactant required to increase the wettability of the composition to a desired level will depend in-part upon the HLB value and level of immobilizing agent, if any, used, the HLB value of the surfactant used and like factors. The composition can comprise from about 0.1 to about 50% of the hydrophilic surfactant when needed to increase the wettability properties of the composition. Preferably, the composition comprises from about 1 to about 25%, most preferably from about 10 to about 20%, of the hydrophilic surfactant when needed to increase wettability.

Compositions can comprise other components typically present in emulsions, creams, ointment, lotions, powders, suspensions, etc. of this type. These components include water, viscosity modifiers, perfumes, disinfectant antibacterial actives, antiviral agents, vitamins, pharmaceutical actives, film formers, deodorants, opacifiers, astringents, solvents, preservatives, and the like. In addition, stabilizers can be added to enhance the shelf life of the composition such as cellulose derivatives, proteins and lecithin. All of these materials are well known in the art as additives for such formulations and can be employed in appropriate amounts in the compositions for use herein.

If water-based skin care compositions are used, a preservative will be needed. Suitable preservatives include propyl paraben, methyl paraben, benzyl alcohol, benzalkonium, tribasic calcium phosphate, BHT, or acids such as citric, tartaric, maleic, lactic, malic, benzoic, salicylic, and the like. Suitable viscosity increasing agents include some of the agents described as effective immobilizing agents. Other suitable viscosity increasing agents include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Suitable solvents include propylene glycol, glycerine, cyclomethicone, polyethylene glycols, hexylene glycol, diol and multi-hydroxy based solvents. Suitable vitamins include A, $D_3$, E, $B_5$ and E acetate.

IX. Treating Articles with Composition

In preparing absorbent articles of the present invention, the skin care composition containing the protease inhibitor is applied such that during wear, at least some portion of the composition will transfer from the treated article to the wearer's skin. That is, skin care composition is either applied directly to one or more wearer contacting surfaces, or is applied in alternate locations or means such that the skin care composition is readily available for transfer from one or more wearer contacting surfaces during use without intervention by the user/caregiver. (For example, materials positioned beneath the wearer contacting surface, encapsulated compositions, etc.) Of course, to effectuate delivery of composition to those body regions most susceptible to contact with feces, it will be preferred to include the composition on the portion of the topsheet and cuffs that will contact the wearer's buttocks, genitals, intertriginous and anal regions during wear. Additionally, the composition may be applied to other article regions for delivery to one or more of the wearer's hips, abdomen, back, waist, sides, thighs, etc. Suitable methods include spraying, printing (e.g., flexographic printing), coating (e.g., contact slot coating, gravure coating), extrusion, or combinations of these application techniques, e.g. spraying the skin care composition on a rotating surface, such as a calendar roll, that then transfers the composition to the desired portion of the article. The skin care composition containing the protease inhibitor can also be applied as a solid material via any of a variety methods, for example extrusion.

When applied to the article's topsheet, the manner of applying the composition to the article should be such that the topsheet does not become saturated with the composition, at least in the region corresponding to the liquid discharge region of the article, if the composition is hydrophobic in nature. If the topsheet becomes saturated with the composition in the liquid discharge region, there is a greater potential for the composition to block the topsheet openings, reducing the ability of the topsheet to transmit liquid to the underlying absorbent core. Also, saturation of the topsheet is not required to obtain the therapeutic and/or protective benefits. Similarly, saturation of other treated article components may not be necessary or desired to transfer sufficient composition for desired skin benefits. Particularly suitable application methods will apply the composition primarily to the outer surface of the topsheet of the article.

The minimum level of the composition containing the protease inhibitor to be applied to the article's wearer-contacting surface is an amount effective for providing the therapeutic, protective and/or skin conditioning benefits when the composition is delivered pursuant to the present invention. The level of composition applied will depend on various factors, including the article component treated, the relative amount of surface area of the wearer-contacting surface not treated with the composition, the composition's content and the like. In general, with compositions that are relatively hydrophobic and are to be applied to essentially all of the topsheet, the composition is preferably applied to the article topsheet in an amount ranging from about 0.1 mg/in$^2$ (0.016 mg/cm$^2$) to about 15 mg/in$^2$ (2.33 mg/cm$^2$), more preferably from about 1 mg/in$^2$ (0.16 mg/cm$^2$) to about 10 mg/in$^2$ (1.55 mg/cm$^2$). It will be recognized that higher levels of skin care composition may be applied to other article components where fluid handling properties are not impacted (e.g., cuffs, waist band, side panels, etc.). It will also be recognized that for compositions that are relatively hydrophilic, higher add-on levels may be used on the topsheet without adversely impacting liquid handling properties to an unacceptable degree. Conversely, higher levels of a hydrophilic composition may be undesired when applied to components (e.g., cuff, waist) other than the topsheet, to avoid wicking of exudates to the edges of the article which may result in leakage.

Because the composition is preferably substantially immobilized on the surface of the region treated, relatively small amounts of composition are needed to deliver an effective amount of the protease inhibitor. It is believed that the ability to use low levels to impart the desired skin benefits is due to the fact that the composition is continuously, automatically delivered as articles are worn. As indicated, the ability to use relatively low levels of skin care composition, allows the article's topsheet to maintain its liquid transfer properties in the liquid discharge region.

The skin care composition containing a protease inhibitor can be applied nonuniformly to the wearer contacting surface of the article. By "nonuniform" it is meant that the amount, location, pattern of distribution, etc. of the composition can vary over the wearer-contacting surface, and may further vary over specific regions of the article. For example, to maintain the liquid handling performance of the topsheet, it may be desired to apply the composition nonuniformly to the topsheet, particularly if the composition is hydrophobic in nature. In this regard, some portions of the treated surface of the article (and regions thereof) can have greater or lesser amounts of composition, including portions of the surface that do not have any composition on it. When the composition is relatively hydrophobic, in one such preferred embodiment the surface of the topsheet will have regions where no composition is applied, particularly in areas of the topsheet that correspond to the crotch region of the article. As used herein, the crotch region of the article is the rectangle, defined below, that is centered longitudinally and laterally about the article's crotch point. The "crotch point" is determined by placing the article on a wearer in a standing position and then placing an extensible filament around the legs in a figure eight configuration. The point in the article corresponding to the point of intersection of the filament is deemed to be the crotch point of the article. (It is understood that the crotch point is determined by placing the absorbent article on a wearer in the intended manner and determining where the crossed filament would contact the article.) With regard to incontinence devices (e.g., diapers, adult incontinent articles), the length of the crotch region corresponds to 40% of the absorbent article's total length (i.e., in the y-dimension). With regard sanitary napkins, the length of the crotch region corresponds to 80% of the absorbent article's total length. The width of the crotch region is equivalent to the width of the widest absorbent core component as measured at the crotch point. (As used herein, "absorbent core" components are those materials involved with acquiring, transporting, distributing and/or storing body liquids. As such, the term absorbent core does not include the topsheet or backsheet of the absorbent article.) By way of illustration, for an incontinent article having a length of 20 in. and a core width at the crotch point of 4 in., the crotch region is the rectangle, centered on the crotch point, having a length of 8 in. and a width of 4 in.

Surprisingly, while the topsheet or other components comprising the protease-containing composition are treated nonuniformly (e.g., microscopic or macroscopic regions where no composition is applied), during wear of the article, the composition is transferred to the wearer even in regions of the skin corresponding to untreated regions within the topsheet or other components. The amount and uniformity of composition transferred to the skin is believed to depend on several factors, including, for example, application pattern of the skin care composition, contact of the wearer's skin to the treated article surface, friction created during wear time between the wearer's skin and the treated region, warmth generated from wearer to enhance the transfer of the composition, the composition's properties, the materials which constitute the composition, and the like.

Where the composition is applied nonuniformly, any pattern may be utilized, including, for example, application of small droplets (obtained via, e.g., spraying) discrete dots (obtained via, e.g., gravure printing), stripes that run in the longitudinal or lateral direction of the article (obtained via contact slot coating), spirals that run in the longitudinal or lateral direction, etc., patterned prints, etc. In those embodiments where the topsheet comprises discrete, untreated regions, the percent open area of the region of the topsheet that corresponds to the crotch region of the article can vary widely. (As referred to herein, the "percent open area" of the topsheet is determined by (i) measuring the surface area of the topsheet that overlies the crotch region, (ii) measuring the total surface area of the untreated region(s) in this portion of the topsheet and (iii) dividing the measurement in (ii) by the measurement in (i). As used herein, "untreated" means a region of the topsheet having less than about 0.01 mg/in$^2$ (0.0016 mg/cm$^2$) of the composition. In this regard, the percent open area may be from about 1% to about 99%, from about 5% to about 95%, from about 10% to about 90%, from about 15% to about 85%, from about 20% to about 80%, from about 25% to about 75%, from about 30% to about 70%, or from about 35% to about 65%. The percent open area required to achieve the desired composition effect and the desired liquid handling properties of the topsheet will be dictated largely by the characteristics of the composition (in particular the composition's contents and its relative hydrophobicity/hydrophilicity properties). One skilled in the art will appreciate that the desired percent open area will be readily determined through routine experimentation.

In general, with compositions that are relatively hydrophobic and are to be applied such that regions of the topsheet are not coated with the composition, the composition is preferably applied to the article topsheet in an amount ranging from about 0.05 mg/in$^2$ (0.0078 mg/cm$^2$) to about 35 mg/in$^2$ (5.43 mg/cm$^2$), more preferably from about 1 mg/in$^2$ (0.16 mg/cm$^2$) to about 25 mg/in$^2$ (3.88 mg/cm$^2$), still more preferably 4 mg/in$^2$ (0.62 mg/cm$^2$) to about 20 mg/in$^2$ (3.1 mg/cm$^2$). It will be recognized that for compositions that are relatively hydrophilic, higher add-on levels may be used without adversely impacting liquid handling properties of the topsheet to an unacceptable degree. Of course, for articles having relatively high percent open areas in the crotch, greater add-on levels may be obtainable without adversely affecting liquid handling by the topsheet.

In one preferred embodiment of the present invention, the topsheet of the articles utilized will comprise stripes of protease-containing composition that run in the article's longitudinal direction. These longitudinal stripes (or spirals) are separated by longitudinal stripes where little or no protease-containing composition is applied to the topsheet. In these embodiments, each stripe of composition will typically have a width of from about 0.1 in. to about 0.75 in., more typically from about 0.1 in. to about 0.5 in., and the width of the stripes containing no composition will typically be from about 0.1 in. to about 1 in., more typically from about 0.15 to about 0.5 in. These ranges are applicable to typical infant diaper designs. For larger products such as adult incontinent products, these ranges may be higher Skin care composition can also be applied in nonuniform patterns on other article components. In these cases, the open area is calculated by the rectangle defined by the perimeters of the skin care composition.

The composition can be applied to the article at any point during assembly. For example, the composition can be applied to the finished disposable absorbent product before it has been packaged. The composition can also be applied to a given component (e.g., topsheet, cuffs, sides, waist, etc.), at the converting site or by the material supplier, before it is combined with the other raw materials to form a finished disposable absorbent product. Again, the composition can be applied to other zones of the article such that the composition will migrate to one or more wearer contacting surfaces during use.

The composition is typically applied from a melt thereof to the article. Since in a preferred embodiment, the composition melts at significantly above ambient temperatures, it is usually applied as a heated composition to the article. Typically, the composition is heated to a temperature in the range from about 35° to about 150° C., preferably from 40° to about 100° C., prior to being applied to the article. The protease inhibitor may be added to the composition prior to or after heating. If added prior to heating, the temperature to which the composition is heated is selected so as not to denature the protease inhibitor. Alternatively, the protease inhibitor may be added to the pre-heated composition when it has cooled to a temperature that does not affect the protease inhibitor but is still sufficiently liquid to be applied to the article. Once the melted composition has been applied to the article, it is allowed to cool and solidify. Preferably, the application process is designed to aid in the cooling/set up of the composition.

In applying compositions to the articles, contact slot coating, spraying, gravure coating, extrusion coating methods are preferred. One such method involves slot coating of the composition on the article's topsheet after the topsheet is assembled with the other raw materials into a finished product.

X. Test Methods

A. Transfer of Skin Care Composition and Protease Inhibitor to Wearer's Skin Overview This method uses a removable skin analog material that is placed on a wearer's skin for a controlled period of time. After the skin analog has been removed, it is extracted using an appropriate solvent and the amount of skin care composition or the amount of protease inhibitor deposited thereon is determined using known analytical methods. The method is described for use with infant diapers comprising skin care compositions containing protease inhibitors, as defined herein. One of skill in the art will recognize the appropriate changes for other skin care compositions, protease inhibitors, absorbent articles, or wearer types.

Subjects

Approximately equal numbers of male and female infants should be selected using the following inclusion and exclusion criteria. Sufficient infants should be selected to ensure that there are at least fifteen subjects per condition and transfer time who complete all aspects of the test.

Inclusion Criteria
a) Healthy infant
b) Caregiver willing to not use lotions, creams, powders or other skin preparations in the diaper area for the duration of the test.
c) Infants who wear disposable diapers full time.

d) Caregiver willing to give child bath the evening before the study and not again until after completion of the study.

e) Caregiver willing to have child refrain from swimming from the evening before the study until after completion of the study.

Exclusion Criteria a. The infant has been ill within the last four days.

b. Diarrhea (soft stool) any time during the four days before the test.

c. Medication which might increase frequency of bowel movements (e.g., oral antibiotics, anti fungal agents, corticosteroids).

d. Damaged skin in or around the test site (e.g., from sunburn, active dermal lesions, or the like).

e. Known allergies or irritation from adhesive or skin care ingredients.

Materials

In Vivo Transfer

| | |
|---|---|
| Skin Analog: | Dermatological Tape - TEGADERM Tape No. 1622W available from 3M Health Cares, St. Paul, MN |
| Sample Container: | Glass jar with closure available from VWR Scientific, West Chester, PA as catalog Number 15900-242 |
| Tape Release Powder: | Baby powder (comprising only talc and fragrance) available from Johnson & Johnson, New Brunswick, NJ |
| Surgical Gloves: | Available from Best Manufacturing Co., Menlo GA, as product 6005PFM. |

Extraction and Analysis of Skin Care Composition

| | |
|---|---|
| Extraction Solvent | Dichloromethane, available from Sigma-Aldrich of St. Louis, MO as 27056-3 |
| Stearyl alcohol | Aldrich 25876-8 |
| 1-Hexadecanol | Aldrich 25874-1 |
| Dispensing Flask | 10 ml |
| Gas Chromatograph | Flame ionization Detector, Hewlett Packard Model 5890 is suitable. |
| Column | Capillary column: Chrompack CP Sil-5 CB, 2 meters × 0.25 mm id, 0.12 micron film thickness fused silica capillary (no substitutions) |
| Instrumental Data | Must be able to reproducibly determine areas of peaks of interest. |

System:
Extraction and Analysis of Protease Inhibitor (Hexamidine)

| | |
|---|---|
| Extraction Solvent: | Dichloromethane, available from Sigma-Aldrich of St. Louis, MO as 27056-3 |
| Dispensing Flask: | 10 mL |
| Column: | Hewlett Packard Zorbax SB-CN narrow bore 5 micron, 2.1 × 150 mm with a Waters Bondapak CN 10 micron, 3.9 × 20 mm guard column. |
| Instrumental Data | Must be able to reproducibly determine areas of peaks of interest. |

System:
Method
In Vivo Transfer

A. Confirm from the subject's caregiver that the subject has been bathed within the last 24 hours and that no lotions, powders, etc. have been applied to the diapered region of the subject's skin since bathing.

B. Wearing the surgical gloves, place the subject on the table and remove his/her diaper.

C. Turn the subject on his/her stomach.

D. Remove the release liner from a TEGADERM tape and lightly brush J&J Baby Powder over the adhesive surface (Wear surgical gloves, or the like, during application to prevent contamination of the tape). Provide sufficient powder such that there is a light coat of powder over all of the tape except the edges. (This step is done to keep the tape from adhering too aggressively to the child's skin.).

Figure 2A:
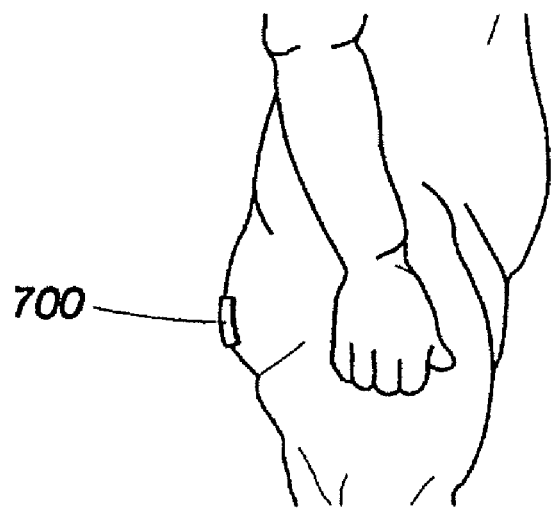
FIG. 2A is a side view showing placement of a skin analog used in the skin care composition transfer test and/or the protease inhibitor transfer test.
Figure 2B:
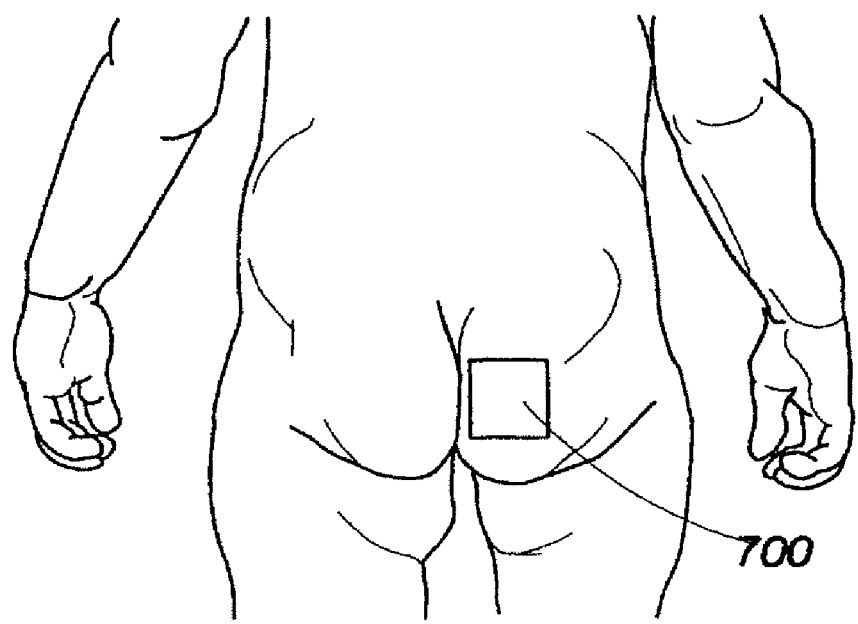
FIG. 2B is a plan view showing placement of the skin analog used in the skin care composition transfer test and/or the protease inhibitor transfer test.

E. FIGS. 2a and 2b illustrate placement location for the TEGADERM tape, shown in those figures as tape 700. Apply the tape 700 to the child's right buttock. The tape 700 is to be applied to the highest point on the child's buttock immediately adjacent to, but not in, the child's gluteal groove. A second tape 700 may be applied to measure transfer at two time increments or the effect of an additional diaper. If a second tape is used, apply the tape 700 on the left buttock using the procedure described above.

F. Change diapers according to the following protocol: 3 hour transfer time—1 diaper; 6 hour transfer time—2 diapers (change at 3 hours); 24 hour transfer times ad lib by caregiver. For 24 hour transfer times the following additional instructions are to be followed:

1. Use only water and a washcloth for cleaning the diapered area for the duration of the test. Do not use baby wipes. Avoid touching the area around the tapes with hands or any cleaning implement.

2. Do not use skin care products (lotions, ointments, creams, soap, etc.) for the duration of the test.

3. Do not bathe the subject for the duration of the test.

4. Use only the test diapers. Record the time of each diaper change.

5. Record the time of any bowel movement and clean the subject with water and a wash cloth.

G. Record the time each diaper was applied for all test diapers.

H. Recall the subject near the end of the predetermined transfer time.

I. Remove the test diaper. If the child has had a bowel movement, the study personnel should remove the tape 700 and discard it (the subject has then completed the test and data from that subject are not included in the analysis). If the subject has urinated, the tape 700 will be acceptable for analysis as described below.

J. Test facility personnel should wear surgical gloves and remove the tape 700 by grasping the edge of the tape 700 with tweezers and gently peeling the remaining portion of the tape 700 from the skin.

K. Make sure the jar is and gently peeling the remaining properly labeled for subsequent sample identification.

L. At the completion of the test collect all of the samples in the jars for analysis as described below.

1. Extraction and Analysis of Test Samples For Skin Care Composition

This method is designed for use with the preferred skin care composition, the skin care composition of Table 4. One of ordinary skill in the art will recognize what adaptions may be necessary to extract and analyze the level of other skin care compositions. In principle: 1) one of the major ingredients of the composition is extracted from the skin analog using an appropriate solvent; 2) gas chromatographic or other appropriate quantitative analytical techniques are then used to determine the level of the major ingredient in the extract; 3) amount of skin care composition is calculated per unit area based on amount of major ingredient in extract and the area of the tape.

Internal Standard/Extraction Solvent

Prepare an internal standard/extraction solvent by accurately weighing 100±2 mg of 1-hexadecanol into a small beaker. Dissolve the 1-hexadecanol in dichloromethane and transfer to a 1 liter volumetric flask. Rinse the beaker 3 more times with dichloromethane transferring each rinse portion to the volumetric flask. Fill the volumetric flask to volume and mix well. This solution will be used to deliver the internal standard and extract skin care composition from the tapes. When not being used, this container should be kept tightly capped to prevent evaporation of solvent.

Calibration Standard

Prepare a calibration standard of known concentration by accurately weighing (±0.1 mg) 10±1 mg of the stearyl alcohol into a 100 ml volumetric flask. Record the weight of stearyl alcohol used. Add the internal standard/extraction solvent to the flask and mix to dissolve. Fill to volume and mix well. When not being used, this container should be kept tightly capped to prevent evaporation of solvent. This solution will be used to determine the relative response of the stearyl alcohol to the 1-hexadecanol internal standard for calibration of the instrument.

Preparation and Calibration of the Gas Chromatograph

All equipment should be installed, operated and maintained according to manufacturer's recommendations.

Install the column and check all the gas flows with the column oven at 100° C. and the injection port and detector at operating temperatures. The GC will be operated under the following conditions:

| | |
|---|---|
| Carrier Gas: | Hydrogen (Helium may be used); flow rate 1.5 ml/min |
| Injection Port: | 325° C.; Split vent flow 30 ml/min; Septum purge 2 ml/min; straight through liner with glass wool plug; Merlin microseal. |
| Injection volume: | 2 μl split |
| FID Detector: | 350° C.; set gas flows according to manufacturer suggestions. Typical gas flows are 400 ml/minute for air, 30 ml/minute for hydrogen and 30 ml/minute for the auxiliary (make up) gas. |
| Column Oven: | 100° C. ramped at 15° C./minute to 325° C.; hold for 10 minutes |

Insure that all connections are tight and leak free. Ignite the detector and allow it to stabilize. Condition the column at 325° C. for 30 minutes. Clean the syringe with dichloromethane as needed. The syringe should also be rinsed with dichloromethane several times after each injection. Make several blank runs with injections of dichloromethane to ensure that a good baseline is obtained and that no extraneous peaks are present in the chromatogram. If extraneous peaks are present or baseline is not suitable, trouble shoot and correct problem(s).

Calibrate the instrument using the calibration standard prepared previously. Consult the data system manufacturer's instructions for the proper sequence of operations. Calculations should be performed in a manner similar to that described in CALCULATIONS below in order to provide the desired result.

Sample Analysis Procedure

1) Remove the lid from the sample jar and add 10 ml of the extraction solvent/internal standard solution using the dispensing flask. Replace the cap and swirl the contents to insure that the tape 700 is not adhering to the sides of the jar and is totally submersed in solvent. Repeat for all samples.
2) Allow the samples to sit 16 hours (typically done overnight).
3) Swirl the contents of the jar to mix. Using a transfer pipette, transfer an aliquot of the sample extract to a properly labeled autosampler vial. Cap the vial. Replace jar lid and retain until analyses are complete. Repeat for all samples.
4) Place the vials in the autosampler in random order and start the analyses using the GC conditions described above. The first vial should be a dichloromethane blank. Several "check" standards should be placed (about every 20th sample) through out the run to verify correct operation.
5) At the completion of the run, check each chromatogram to insure proper analysis. If a problem is suspected, trouble shoot and correct. Reanalyze samples as needed.

Calculations

The total micrograms of stearyl alcohol in each sample extract is calculated based on the relative response of the stearyl alcohol peak to that of the 1-hexadecanol internal standard. The ratio of the peak areas is multiplied by the relative response factor (determined at time of instrument calibration) and the micrograms of internal standard in the extract to yield the total μg of stearyl alcohol in a sample.

Instrument Calibration

Determine the instrumental relative response factor for the stearyl alcohol and the internal standard based on the areas of the stearyl alcohol and 1-hexadecanol peaks in the calibration standard chromatogram.

$$\text{Response factor } (Rf) = \frac{Area_{inst}}{weight_{inst}} \times \frac{weight_{sa}}{Area_{sa}} \times 10$$

where:
$Area_{inst}$=GC peak area for the internal standard
$Area_{sa}$=GC peak area for the stearyl alcohol
$weight_{inst}$=micrograms of the internal standard used to prepare internal standard/extraction solvent
$weight_{sa}$=micrograms of the stearyl alcohol used to prepare the calibration standard Sample Calculations Calculate the total micrograms of stearyl alcohol in each sample using the peak areas from the sample chromatogram in the following equation:

$$\text{Total } \mu_g \text{ } SA = \frac{Area_{sa}}{Area_{inst}} \times R_f \times \frac{weight_{inst}}{100}$$

where: $Area_{inst}$=GC peak area for the internal standard
$Area_{sa}$=GC peak area for the stearyl alcohol
$weight_{inst}$=micrograms of the internal standard used to prepare internal standard/extraction solvent Report amount of skin care composition transferred in mg/cm² where:

Composition Transferred =

$$\frac{0.001 \times \mu g \text{ of stearyl alcohol}}{\text{(concentration of stearyl alcohol in composition)} \times \text{(tape area)}}$$

For the method described above the concentration of stearyl alcohol in the composition is 41% and the tape patch measures 4.4 cm×4.4 cm.

$$\text{Composition Transferred} = \frac{(0.001 \times \mu g \text{ of stearyl alcohol})}{(0.41 \times 4.4 \text{ cm} \times 4.4 \text{ cm})}$$

$$= 0.126 \times \mu g \text{ of stearyl alcohol}(mg/cm^2)$$

2. Extraction and Analysis of Test Sample for Protease Inhibitor

This method is designed for use with the skin care composition containing a protease inhibitor of Table 1. One of ordinary skill in the art will recognize what adaptations may be necessary to extract and analyze the level of other protease inhibitors. In principle: 1) the protease inhibitor is extracted from the skin analog using an appropriate solvent; 2) HPLC or other quantitative analytical techniques are then used to determine the level of the inhibitor in the extract; 3) the amount of a protease inhibitor is calculated per unit area based on the amount of inhibitor in the extract and the area of the tape.

Preparation of Standards

To prepare a 10 ug/mL standard solution of hexamidine, weigh 0.10 grams+/−0.02 grams of reagent grade hexamidine diisethionate and dissolve this in an HPLC mobile phase (10% glacial acetic acid and 17.5% methanol) solution. Prepare additional hexamidine standards by aliquoting the 10 ug/mL standard solution as shown in Table 3 and diluting to volume in 100 mL flasks with the HPLC mobile phase solution.

TABLE 3

Standards Preparation*

| Standard | mL hexamidine standard solution | Final Volume (mL) | Nominal Conc. (ug/mL) |
|---|---|---|---|
| 1 | 5.0 | 100 | 0.5 |
| 2 | 10.0 | 100 | 1.0 |
| 3 | 25.0 | 100 | 2.5 |
| 4 | 50.0 | 100 | 5.0 |

Sample Preparation

1. Place the transfer tape sample in a 40 mL glass vial.
2. Add 10 mL of dichloromethane to the vial using a dispensing flask, and cap the vial tightly.
3. Secure the vial in wrist-action shaker and shake for 30 minutes.
4. Remove the vial from the shaker, remove the cap of the vial and add 10 mL of the HPLC mobile phase solution to the vial. Re-cap the vial and place the vial securely in the wrist-action shaker.
5. Shake the sample for 30 minutes to dissolve the hexamidine in the aqueous phase.
6. Allow the vial/sample to sit and the layers to separate for a least 30 minutes before proceeding.
7. After the sample has separated, remove the aqueous (top layer) from the vial with a disposable syringe and filter the aqueous phase through a 0.45 micron filter into a HPLC sample vial.

Sample Analysis

1. Chromatograph the standards and the samples under the conditions described in Table 4.

TABLE 4

| Chromatographic Conditions | |
|---|---|
| Mobile Phase Flow Rate: | 0.25 mL/min. |
| Mobile Phase: | 10% glacial acetic acid, 17.5% methanol |
| Injection Volume: | 10 mL |
| UV Detector Wavelength: | 254 nm |
| UV Detector Sensitivity: | 1.000 AUFS |
| UV Detector Filter: | 2.0 sec |
| Run Time: | 10.0 min |

Calculations

1. Standard concentration (mg/mL):

$$S_i(mg/mL) = W(mg)/100 * (V_1/100) \quad (1)$$

W=weight of hexamidine for stock standard solution
$V_1$=volume of hexamidine stock solution used to prepare the standard (Table I)

2. Calibration Curve
    A. Tabulate mg/mL of hexamidine in each standard ($S_i$) and the responses (peak areas or peak heights), $R_i$, for each of the standard solutions.
    B. Construct a calibration curve by performing a least-squares fit of equation 2 to the data.

$$R_i = mS_i + b \quad (2)$$

3. Test Samples
    A. Calculate the amount of Hexamidine ($H_1$) in sample extracts using the measured response R and the calibration equation:

$$H_1 = (R-b)/m \quad (3)$$

B. Calculate the amount of Hexamidine (H) in samples in mg according to eq. 4.

$$H = H_1 * 10 \quad (4)$$

C. Divide the amount of hexamidine (H) by the tape area to determine the concentration of hexamidine per unit area of skin analog.

VII. SPECIFIC EXAMPLES

The following are specific illustrations of (a) treating diaper topsheets with skin care compositions and (b) methods of the present invention which utilize articles comprising those topsheets. Similar approaches may be utilized to treat other components for providing treated articles for use in the present methods.

Example 1

Preparation and Testing of an Absorbent Article Having a Topsheet Comprising a Skin Care Composition and a Protease Inhibitor A. Preparation of Skin Care Composition A skin care composition (Composition A) is made by mixing the following components together: (i) 99 parts of a melted (i.e., liquid) base composition containing 58 parts petrolatum (available from Witco Corp., Greenwich, Conn. as White Protopet); 41 parts stearyl alcohol (available from Procter and Gamble Co., Cincinnati, Ohio as CO1897); and 1 part aloe extract (available from Madis Botanicals, Inc., S. Hackensack, N.J. as Veragel Lipoid in Kaydol), with (ii) 1 part hexamidine diisethionate (available from Laboratories Serobilogiques, Pulnoy, France as Elestab HP100).

B. Preparation of a Treated Article by Contact Slot Coating

Composition A is placed into a heated tank operating at a temperature of 170° F. The composition is subsequently applied with a contact applicator (using, for example, a Meltex EP45 hot melt adhesive applicator head having 5 slots and operating at a temperature of 170° F.) onto the topsheet of an article in a striped pattern where the stripes run in the article's longitudinal direction. Specifically, 5 stripes are applied, each stripe measuring 0.25 in. wide (i.e., in the articles lateral direction) and 11.75 in. long at an add-on level=7.7 mg/in$^2$ (12 g/m$^2$, 1.19 mg/cm$^2$). The distance between the stripes is 0.31 in.

C. Testing of a Treated Article for Enzyme Inhibition Property

This Example describes a method of testing a diaper for a protease inhibitory activity. It is not intended to be limiting, as other portions of other absorbent articles can be sampled and other methods employing other extraction solvents and other substrates systems and the like can be used for testing.

Ten random ¾ inch punches are made in the core area of the absorbent article treated with Composition A, as described in Section B above, and in a control article not containing any inhibitor. Each of the punched areas is then tested for trypsin inhibition activity as follows: The topsheet is removed from the punch and placed in a 1.5 mL centrifuge vial. The sample is soaked overnight in 0.75 mL water. An aliquot (0.125 mL) of the supernatant liquid is removed and added to a cuvette containing 0.025 mL of 160 nM human pancreatic trypsin in TRIS-HCl containing 20 mM CaCl$_2$, pH 8.2, and incubated for 10 minutes at 25° C. Cbz-arginine-p-nitroanilide substrate (0.025 mL of a 4 mM solution) is added to each cuvette and the test and control samples are incubated for 5 minutes. The change in absorbance at 405 nm for each sample is then monitored over 10 minutes. The assay results illustrated in Table 5 indicate the absorbent article containing the inhibitor causes a reduction in the trypsin activity measured (relative to a control article which is identical except that it contains no inhibitor) and is an article of the present invention.

TABLE 5

| | OD change/min × 10$^{-3}$ |
|---|---|
| Control Article | 8.292 ± 0.6 |
| Example 2 Article | 3.804 ± 2 |

Example 2

Method of Improving Skin Health

An active incontinent adult weighing 165 lbs. who constantly uses absorbent articles and who persistently has mild erythema uses an adult incontinent product analogous to the diaper of Example 1 for a period of at least about 5 days. The subject's article is changed according to the routine patterns of the user. (Typical changing patterns consist of changes every four to five hours during the day and application of a fresh article before overnight sleep.) No intervention by the user, in the form of manual application of any type of skin protective or moisture repellent or diaper rash treatment products, occurs during this period. At the end of the 5 day period, the subject is observed to have reduced or resolved erythema.

Example 3

Method of Improving Skin Health

An infant weighing 32 lbs. exhibiting mild diaper rash and erythema is diapered for a period of at least about 5 days using the diaper of Example 1 during overnight sleep only. (That is, an untreated article is used throughout the day.) The infant's diaper is changed according to the routine patterns of the caregiver. No intervention by the caregiver, in the form of manual application of skin protective or moisture repellent or diaper rash treatment products, occurs during this period. At the end of the 5 day period, the subject is observed to have reduced or resolved rash and erythema.

Example 4

Method of Maintaining Skin Health

An infant weighing 25 lbs. exhibiting no diaper rash or erythema is diagnosed with otitis media and is prescribed a course of systemic antibiotics. Based on experience with conventional (untreated) diapers, the caregiver expects that the infant will develop erythema and/or diaper rash resulting from loose stools. As a result, diapers such as that described in Example 1 are used continuously throughout the period of administration of the antibiotic. No intervention by the caregiver, in the form of manual application of skin protective or moisture repellent or diaper rash treatment products, occurs during this period. Throughout the period of antibiotic administration, the subject exhibits no erythema or diaper rash.

The disclosures of all patents, patent applications (and any patents which issue thereon, as well as any corresponding published foreign patent applications), and publications mentioned throughout this description are hereby incorporated by reference herein. It is expressly not admitted, however, that any of the document incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, at least a portion of which comprises a protease inhibitor selected from the group consisting of soybean trypsin inhibitor; lima bean protease inhibitor; corn protease inhibitor; Bowman Birk inhibitor; human pancreatic trypsin inhibitor; bovine pancreatic basic trypsin inhibitor; egg white trypsin inhibitor; ovomucoids containing ovoinhibitors; chymostatin; aprotinin; bestatin and its analogs; amastatin and its analogs; antipain; antithrombin III; hirudin; cystatin; 4-sulfamoylphenyl-4-guanidinobenzoate methanesulfonate; camostat; elafin; E-64 and its analogs; $\alpha_2$-macroglobulin; $\alpha_1$-antitrypsin; pepstatin and its analogs; apstatin; (2R)-2-mercaptomethyl-4-methylpentanoyl-b-(2-naphthyl)-Ala-Ala amide; (2R)-2-mercaptomethyl-4-methylpentanoyl-Phe-Ala amide; N-acetyl-Leu-Leu-methioninal; N-acetyl-Leu-Leu-norleucinal; p-aminobenzoyl-Gly-Pro-$_D$-Leu-$_D$-Ala hydroxamic acid; 2(R)-[N-(4-methoxyphenylsulfonyl)-N-(3-pyridylmethyl)amino]-3-methylbutano-hydroxamic acid; p-aminobenzamidine and its salts and derivatives; guanidinobenzoic acid and its salts and derivatives; and mixtures thereof.

2. The absorbent article of claim 1, wherein said absorbent article comprises from about 0.0001% to about 30%, by weight of said absorbent article, of said protease inhibitor.

3. The absorbent article of claim 2, wherein said absorbent article comprises from about 0.0001% to about 10%, by weight of said absorbent article, of said protease inhibitor.

4. The absorbent article of claim 1, wherein said protease inhibitor is present as a powder, a flake, a particle, a solution, a suspension, a dispersion, an emulsion, or mixtures thereof.

5. The absorbent article of claim 1, wherein the portion of said absorbent article is selected from the group consisting of a liquid impervious backsheet, a liquid pervious topsheet, an absorbent core positioned between the topsheet and the backsheet, a secondary layer underlying the topsheet or the absorbent core, and combinations thereof.

6. The absorbent article of claim 1, further comprising a delivery system for containing said protease inhibitor and delivering said protease inhibitor to at least a portion of the skin of a wearer of said absorbent article.

7. The absorbent article of claim 6, wherein said delivery system comprises a microcapsule, an absorbent material, a cell, an adhesive, a skin care composition, a nanophase particulate structure, a solid support, or combinations thereof.

8. The absorbent article of claim 6, wherein said delivery system is activatable by moisture, heat, pressure, or combinations thereof, and wherein said delivery system releases said protease inhibitor when activated.

9. The absorbent article of claim 6, wherein said delivery system contains said protease inhibitor as a powder, a flake, a particle, a solution, a suspension, a dispersion, an emulsion, or combinations thereof.

10. The absorbent article of claim 6, wherein said delivery system is a component of a portion of the article selected from the group consisting of a liquid impervious backsheet, a liquid pervious topsheet, an absorbent core positioned between the topsheet and the backsheet, a secondary layer underlying the topsheet or the absorbent core, and combinations thereof.

11. The absorbent article of claim 6, wherein said delivery system is a skin care composition wherein said skin care composition comprises from about 0.01% to about 50%, by weight of said skin care composition, of said protease inhibitor, wherein at least a portion of said skin care composition is transferred from the article to a wearer's skin during wear of said absorbent article.

12. The absorbent article of claim 11, wherein said skin care composition comprises from about 0.05% to about 25%, by weight of said skin care composition, of said protease inhibitor.

13. The absorbent article of claim 11, wherein said skin care composition comprises from about 0.1% to about 10%, by weight of said skin care composition, of the protease inhibitor.

14. The absorbent article of claim 1, wherein said absorbent article comprises a wearer-contacting surface, wherein a skin care composition containing said protease inhibitor is disposed on at least a portion of said wearer-contacting surface.

15. The absorbent article of claim 14, wherein said wearer-contacting surface is a topsheet.

16. The absorbent article of claim 15, wherein said topsheet comprises one or more regions that do not contain said skin care composition containing said protease inhibitor.

17. The absorbent article of claim 16, wherein said skin care composition containing said protease inhibitor is contained on said topsheet in the form of a plurality of stripes that are separated by a plurality of stripes having no skin care composition.

18. The absorbent article of claim 1, wherein said absorbent article comprises a topsheet, a backsheet, and an absorbent core disposed between said topsheet and said backsheet, wherein said protease inhibitor is disposed on said absorbent core of said absorbent article.

* * * * *